US010638638B2

(12) United States Patent
Augustine et al.

(10) Patent No.: US 10,638,638 B2
(45) Date of Patent: *Apr. 28, 2020

(54) RELOCATION MODULE FOR PATIENT MONITORS AND SURGICAL EQUIPMENT

(71) Applicant: Augustine Biomedical + Design, LLC, Eden Prairie, MN (US)

(72) Inventors: Scott D. Augustine, Deephaven, MN (US); Susan D. Augustine, Deephaven, MN (US); Garrett J. Augustine, Deephaven, MN (US); Brent M. Augustine, Savage, MN (US); Ryan S. Augustine, Minneapolis, MN (US); Randall C. Arnold, Minnetonka, MN (US)

(73) Assignee: Augustine Biomedical + Design, LLC, Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/529,283

(22) Filed: Aug. 1, 2019

(65) Prior Publication Data

US 2019/0357382 A1    Nov. 21, 2019

Related U.S. Application Data

(63) Continuation of application No. 15/935,524, filed on Mar. 26, 2018, now Pat. No. 10,512,191.

(51) Int. Cl.
*A61M 16/18*      (2006.01)
*A61M 16/06*      (2006.01)
(Continued)

(52) U.S. Cl.
CPC ......... *H05K 7/20127* (2013.01); *A61B 90/37* (2016.02); *A61G 13/1235* (2013.01);
(Continued)

(58) Field of Classification Search
CPC .. B01D 46/0093; A61G 13/108; A61M 16/18; A61M 16/06; A61M 16/0051;
(Continued)

(56) References Cited

U.S. PATENT DOCUMENTS

| 4,531,956 A | * | 7/1985 | Howorth | ............ A61G 13/108 454/187 |
| 5,399,007 A | | 3/1995 | Marconet | |

(Continued)

FOREIGN PATENT DOCUMENTS

WO    WO-2019191081 A1    10/2019

OTHER PUBLICATIONS

U.S. Appl. No. 15/935,524, filed Mar. 26, 2018, Relocation Module for Patient Monitors and Surgical Equipment.
(Continued)

*Primary Examiner* — Minh Chau T Pham
(74) *Attorney, Agent, or Firm* — Schwegman Lundberg & Woessner, P.A.

(57) ABSTRACT

A module for housing electronic and electromechanical equipment and for managing waste heat during surgery. The module including a lower section configured to house unrelated waste heat-producing electronic and electromechanical surgical equipment during surgery and a tower-like upper section located above the lower section. A rear portion of the lower section is configured to fit into an unused space under an arm-board of a surgical table. The upper section is configured to be positioned adjacent an anesthesia side of an arm-board of the surgical table and the upper section is configured to accommodate mounting of equipment controls and a display at a height to be viewed and operated by a user.

25 Claims, 21 Drawing Sheets

(51) Int. Cl.
| | |
|---|---|
| *A61B 50/13* | (2016.01) |
| *A61B 46/10* | (2016.01) |
| *A61B 90/50* | (2016.01) |
| *H05K 7/20* | (2006.01) |
| *H05K 5/00* | (2006.01) |
| *H05K 5/02* | (2006.01) |
| *A61B 90/00* | (2016.01) |
| *A61G 13/12* | (2006.01) |
| *A61M 16/00* | (2006.01) |
| *A61M 16/01* | (2006.01) |

(52) U.S. Cl.
CPC ........ *A61M 16/0051* (2013.01); *A61M 16/01* (2013.01); *H05K 5/0021* (2013.01); *H05K 5/0213* (2013.01); *H05K 7/20145* (2013.01); *H05K 7/20181* (2013.01); *A61B 2217/005* (2013.01); *A61B 2218/008* (2013.01); *A61M 2205/18* (2013.01); *A61M 2205/581* (2013.01); *A61M 2205/583* (2013.01); *H05K 5/0017* (2013.01); *H05K 5/0234* (2013.01)

(58) Field of Classification Search
CPC ........ A61M 16/01; A61B 50/16; A61B 50/13; A61B 2050/155; A61B 2205/18; A61B 2205/581; A61B 2218/008; A61B 46/10; A61B 90/50; A61B 90/37
USPC ... 55/385.1, 385.2, 383, 473, 356, 467, 482, 55/DIG. 34; 606/1; 128/898; 96/417–423
See application file for complete search history.

(56) References Cited

U.S. PATENT DOCUMENTS

| | | | | |
|---|---|---|---|---|
| 5,409,511 | A * | 4/1995 | Paul | A61B 18/00 55/383 |
| 5,516,313 | A | 5/1996 | Lumpkin | |
| 5,695,536 | A | 12/1997 | Fabrizi | |
| 7,597,731 | B2 | 10/2009 | Palmerton et al. | |
| 7,674,436 | B1 | 3/2010 | Feldman et al. | |
| 7,753,977 | B2 | 7/2010 | Lyons et al. | |
| 9,603,956 | B2 | 3/2017 | Newham | |
| 10,507,153 | B2 | 12/2019 | Augustine et al. | |
| 10,512,191 | B2 | 12/2019 | Augustine et al. | |
| 2001/0035702 | A1 | 11/2001 | Murphy et al. | |
| 2003/0033790 | A1 | 2/2003 | Hague | |
| 2003/0150328 | A1 | 8/2003 | Hansson et al. | |
| 2004/0103789 | A1 | 6/2004 | Lan et al. | |
| 2005/0060974 | A1* | 3/2005 | Palmerton | A61B 18/00 55/482 |
| 2005/0097870 | A1 | 5/2005 | Moshenrose | |
| 2006/0042205 | A1* | 3/2006 | Kalous | F24F 3/1607 55/385.1 |
| 2007/0199287 | A1 | 8/2007 | Wiser | |
| 2007/0225690 | A1* | 9/2007 | Sekiguchi | A61B 90/50 606/1 |
| 2008/0173178 | A1 | 7/2008 | Metteer | |
| 2010/0094262 | A1* | 4/2010 | Tripathi | A61B 3/14 606/1 |
| 2010/0324380 | A1 | 12/2010 | Perkins et al. | |
| 2011/0030560 | A1 | 2/2011 | Bohlen et al. | |
| 2012/0024154 | A1 | 2/2012 | Augustine et al. | |
| 2012/0305787 | A1 | 12/2012 | Henson | |
| 2013/0243647 | A1 | 9/2013 | Garner et al. | |
| 2014/0262553 | A1 | 9/2014 | Pollock et al. | |
| 2015/0168207 | A1 | 6/2015 | Pollock et al. | |
| 2015/0224237 | A1 | 8/2015 | Reasoner et al. | |
| 2017/0112954 | A1 | 4/2017 | Dayton | |
| 2017/0209658 | A1 | 7/2017 | Tobia et al. | |
| 2019/0105120 | A1 | 4/2019 | Norman et al. | |
| 2019/0290524 | A1 | 9/2019 | Augustine et al. | |
| 2019/0297745 | A1 | 9/2019 | Augustine et al. | |

OTHER PUBLICATIONS

U.S. Appl. No. 16/364,884, filed Mar. 26, 2019, Relocation Modules and Methods for Surgical Field.
"U.S. Appl. No. 15/935,524, Corrected Notice of Allowability dated Jul. 18, 2019", 2 pgs.
"U.S. Appl. No. 15/935,524, Non Final Office Action dated Mar. 8, 2019", 8 pgs.
"U.S. Appl. No. 15/935,524, Non Final Office Action dated Sep. 19, 2018", 8 pgs.
"U.S. Appl. No. 15/935,524. Notice of Allowance dated Jun. 12, 2019", 9 pgs.
"U.S. Appl. No. 15/935,524, Response filed May 15, 2019 to Non Final Office Action dated Mar. 8, 2019", 10 pgs.
"U.S. Appl. No. 15/935,524, Response filed Dec. 12, 2018 to Non Final Office Action dated Sep. 19, 2018", 18 pgs.
"U.S. Appl. No. 16/364,884, Non Final Office Action dated Jul. 3, 2019", 9 pgs.
"U.S. Appl. No. 16/364,884, Response filed Jun. 18, 2019 to Restriction Requirement dated May 1, 2019", 9 pgs.
"U.S. Appl. No. 16/364,884, Response filed Jul. 24, 2019 to Non Final Office Action dated Jul. 3, 2019", 9 pgs.
"U.S. Appl. No. 16/364,884, Restriction Requirement dated May 1, 2019", 5 pgs.
"International Application Serial No. PCT/US2019/024054, Invitation to Pay Additional Fees dated May 29, 2019", 3 pgs.
"U.S. Appl. No. 15/935,524, Corrected Notice of Allowability dated Aug. 21, 2019", 2 pgs.
"U.S. Appl. No. 16/364,884, Corrected Notice of Allowability dated Aug. 29, 2019", 3 pgs.
"U.S. Appl. No. 16/364,884, Corrected Notice of Allowability dated Nov. 8, 2019", 3 pgs.
"U.S. Appl. No. 16/364,884, Notice of Allowance dated Aug. 20, 2019", 10 pgs.
"U.S. Appl. No. 16/601,924, Non Final Office Action dated Dec. 5, 2019", 6 pgs.
"International Application Serial No. PCT/US2019/024054, International Search Report dated Jul. 25, 2019", 5 pgs.
"International Application Serial No. PCT/US2019/024054, Written Opinion dated Jul. 25, 2019", 7 pgs.
"U.S. Appl. No. 16/519,677, Non Final Office Action dated Nov. 13, 2019", 6 pgs.
"U.S. Appl. No. 16/519,677, Response filed Dec. 17, 2019 to Non Final Office Action dated Nov. 13, 2019", 9 pgs.

* cited by examiner

RELOCATION MODULE FOR PATIENT MONITORS AND SURGICAL EQUIPMENT

PRIORITY

This application is a continuation of U.S. patent application Ser. No. 15/935,524, filed Mar. 26, 2018, which is incorporated by reference herein in its entirety.

TECHNICAL FIELD

This document pertains generally, but not by way of limitation, to systems and methods for creating safe operating rooms. In particular, the systems and methods described herein may include but are not limited to, equipment storage, waste air management, and cable and hose management.

BACKGROUND

Anesthesia monitors and equipment as well as surgical equipment have been invented, developed and sporadically introduced into surgical practice over more than a century. This equipment is made by a wide variety of companies who have no incentive to coordinate with one another to create the most efficient operating room. Equipment throughout the operating room has been placed in one location or another, generally without a plan and then decades later, is still sitting in that unplanned location. For example, the first of the electronic monitors used during anesthesia was the electrocardiogram (ECG or EKG), which was introduced into the operating room in the 1960's. When EKGs became small enough to be placed on a shelf, getting it off of the floor, the most available shelf space somewhat near the patient, was above the anesthesia gas machine. As more anesthesia related electronic monitors were developed and introduced into practice over the next 40 years, they were simply stacked on top of one another on the same shelf above the anesthesia machine. Soon it was simply tradition that dictated that vital sign patient monitors are located over the anesthesia machine. Eventually the independent anesthesia related monitors were consolidated into single units for convenience. These consolidated multifunction anesthesia monitors were still placed on the same shelf above the anesthesia machine or on a mounting bracket attached to the anesthesia machine.

Just because a shelf happens to be available does not mean that the anesthesia related monitors are ideally located. The anesthesia machine is generally located to the side of and slightly behind the anesthetist, when standing at the head end of the surgical table facing the patient. In many cases, the anesthesia machine is located behind the anesthetist. Therefore, it is axiomatic that looking at or adjusting the anesthesia related monitors means that the anesthetist is not looking at the patient but rather looking away from the patient. Therefore, when the patient is experiencing a problem and the anesthesia related monitors are reporting confusing or adverse information, the anesthetist is focused away from the patient.

When the anesthesia related monitors are located in their present location over the anesthetic gas machine, the numerous wires, cables and hoses connecting the monitors to the patient are generally 10-12 feet long. There is a minimum of 5 wires and 2 hoses and frequently as many as 10 wires, cables and 2 hoses connecting the monitors to the patient. Electric patient warming blankets, mattresses and fluid warmers are also rapidly gaining acceptance. The controller for the electric warming products is generally located adjacent the anesthesia machine and the 3-6 cables connecting the controller to the warming blankets and mattresses on the patient are 12-15 feet long. Cables and hoses tangled and laying on the floor are clearly a problem in the operating room, causing not only inconvenience but getting contaminated and causing a tripping hazard for operating room personnel.

Cable and hose management on the surgical side of the anesthetic screen (e.g., sheet perpendicular to the table across the neck region of a patient) is also a problem that has developed haphazardly over the past century. Numerous pieces of surgical equipment have been parked somewhat randomly in the middle of the operating room, each causing an obstruction to traffic flow. Each of these pieces of equipment has a power cord or hose that lays on the floor extending to the wall outlet. Each of these pieces of equipment has one or more cables and/or hoses that lays on the floor extending to the sterile field of the surgical table. Every cable and hose on the floor is a hazard for tripping operating room personnel. Every cable and hose on the floor is an obstruction for other rolling equipment and carts and is at risk of damage from these carts, needing replacement.

A typical operating room (OR) has numerous alarms that monitor the patient's vital signs during a procedure, like heart rate and blood pressure, but the complication of multiple alarms ringing simultaneously, and frequent false positives creates a very distracting OR environment.

The various equipment such as electrosurgical units, smoke evacuation pumps, sequential compression sleeve pumps, blood/fluid suction units, and air mattress pumps are scattered about the operating room creating their own obstacles. Wherever the surgical equipment is located in the operating room on the surgical side of the anesthesia screen, the cables and hoses traverse to the sterile field on the surgical table by way of laying on the floor and becoming obstacles.

Waste heat and air discharged from heater-cooler units (HCU) near the floor can form into convection currents of rising warm air and mobilize bacteria up and into the sterile surgical field.

Flow-boundary layers of still air form next to the surgeons and anesthesia screen, preventing the downward airflow from even the best operating room ceiling ventilation systems from reaching the sterile field. When the ventilation airflow slows, the airborne contaminants and bacteria have the opportunity to settle into the open wound.

In some situations, oxygen and alcohol vapors trapped under the surgical drape pose a burn hazard to the patient in the presence of an electro-cautery spark.

SUMMARY

The modules, systems and methods described herein overcome various problems in the operating room. For example, like the cockpit of the fighter plane, the electronic monitors used during anesthesia and surgery should be located near the patient so that the anesthetist's field of vision simultaneously includes: the patient, the monitors and the surgical procedure. However, this is not the case in conventional operating rooms. The modules, systems and method described herein, overcome this and other problems in the operating room, creating a safer environment for the patient and the operating room personnel.

It would also be advantageous if the surgical support equipment and their cables, cords and hoses could be removed from the floor of the operating room.

A reduction of noises and interruptions associated with alarms meant to signal anesthesiologists, that frequently result in distractions to other OR personnel, would be beneficial.

A way of eliminating flow-boundary dead zones from obstructing the ventilation airflow and thus keeping the airborne contaminants and bacteria airborne and out of the wound, would be useful to protect the open wound from airborne contamination.

Waste heat and air discharged from heater-cooler units (HCU) near the floor can form into convection currents of rising warm air and mobilize bacteria up and into the sterile surgical field. Similar contamination of the sterile field with bacteria and contaminates from the floor has been shown in many studies of the waste heat and air from forced-air warming devices. The US Centers for Disease Control has warned that due to the positive link to implant infections, "Nothing that blows air should be in an operating theater, if possible." and " . . . it is important not to blow air in the operating theater." Therefore, there is a need to safely manage waste heat and air from surgical equipment and monitors in order prevent contamination of the sterile surgical field.

With regard to flammable alcohol and oxygen vapors concentrating in particular areas of the OR, eliminating the alcohol vapors and oxygen trapped under the surgical drape would add to the fire safety of the surgical experience.

Illustrative embodiments of a relocation module systematizes surgical safety for patients and OR personnel. In some embodiments, this module designed to house nearly all of the operating room patient monitors and support equipment. Even dissimilar types of equipment that are normally kept separate from one another. In some embodiments, this unique module is specially designed to fit next to and under the arm-board of the surgical table-a location traditionally occupied by an IV pole. For the past 100 years, this location has been a wasted "no-man's land" between the anesthesia and surgical sides of the operating room. In reality, the unique space next to and under the arm-board, is truly the "prime real estate" of the entire operating room: it is immediately adjacent the patient for optimal monitoring while simultaneously maintaining observation of the patient and surgical procedure; equipment controls can be conveniently accessed by both the anesthesia and surgical staff; short cables and hoses are adequate to reach the patient; and it is uniquely accessible from both the anesthesia and surgical sides of the anesthesia screen. The unique space next to and under the arm-board is the only location in the entire operating room where cables, cords and hoses from both the anesthesia side and the sterile surgical field side, do not need to traverse the floor or even touch the floor in order to connect to their respective monitor or patient support equipment-truly a remarkable location that has been wasted by conventional systems.

In some embodiments, an illustrative relocation module can house both anesthesia related and non-anesthesia related equipment. In some embodiments, the illustrative relocation module can house a variety of non-proprietary OR equipment such as patient vital sign monitors and electro-surgical generators. In some embodiments, the module is designed to also house newer proprietary safety equipment such as: air-free electric patient warming, surgical smoke evacuation, waste alcohol and oxygen evacuation, evacuation of the flow-boundary dead-zones that cause disruption of the OR ventilation and the evacuation and processing of waste heat and air discharged from OR equipment. In some embodiments, this module may also house dissimilar equipment (e.g., unrelated to anesthesia monitoring) such as: air mattress controls and air pumps; sequential compression legging controls and air pumps; capacitive coupling electrosurgical grounding: RFID counting and detection of surgical sponges; the waste blood and fluid disposal systems; and "hover" mattress inflators. Any of these devices may be stored in the relocation module together with (or without) anesthesia equipment.

In some embodiments, the relocation module is a specialized and optimally shaped rack for holding and protecting the patient monitors and other electronic and electromechanical surgical equipment, in a unique location. A location that is very different from just setting anesthesia monitors on top of the anesthesia machine and scattering other equipment across the floor of the operating room.

In some embodiments the preferred new location is adjacent the anesthesia side of one or the other of the outstretched arm-boards of the surgical table, a location currently occupied by an IV pole on a rolling stand. In this location, the relocated monitor screens are 1-2 feet lateral to the patient's head, allowing the anesthesia related monitors, the patient and the surgical field to be observed by the anesthetist in a single field of vision. In some embodiments, with the monitors, the patient and the surgical field to be observed by the anesthetist in a single field of vision, it is highly likely that the anesthetist will be looking in that direction most of the time. Because the anesthetist is naturally looking toward the patient and monitors, a relatively bright warning light mounted on the tower or on one of the monitors that are mounted on the tower in this field of vision and aimed at the anesthetist, may be substituted for an audible alarm. The unique location of the tower on the module allows this warning light to be aimed away from the surgical field and it is therefore not distracting or even visible to the surgeon. Only if the warning light is ignored by the anesthetist, would a backup audible alarm which is distracting to the surgeon and OR staff be necessary.

Locating the module adjacent the arm-board has several advantages. First, that space is currently occupied by an IV pole, so it is not currently being used for personnel traffic. Second, the arm-board and the anesthesia screen above the arm-board, traditionally are the separation boundary between the anesthesia side of the operating room and the surgical side of the operating room-essentially an empty "no-man's land" between the two sides. The raised head end of the surgical drape that is tethered between two IV poles, creates a physical barrier between the anesthetist and the surgical field, is commonly known as the "anesthesia screen" or "ether screen." As a "no-man's land," the space under the arm-board is currently unoccupied. The space under the arm-board is unique in that it can be accessed from both the surgical and the anesthesia sides of the anesthesia screen. Access to the module from the surgical side can be from below the lower edge of the surgical drape hanging down over the arm board, or more conveniently from the side of the module facing away from the patient, at the distal end of the arm-board. There is no other location in the operating room that can be simultaneously accessed from both the surgical and anesthesia staff, while maintaining the traditional boundary or "no-man's land" between the two. Therefore, this location is uniquely suited for a module that can contain both surgical and anesthesia equipment.

In some embodiments, locating the module adjacent the arm-board means that one of the side faces of the module is facing the patient and is within 24 inches of the patients' head and chest. This location close to the patient allows for a cable and hose management system with relatively short cables and hoses, which are much easier to manage than long cables and hoses. The traditional long cables and hoses that need to reach from the patient to the electronic monitors located on top of the anesthesia machine by way of draping to the floor, are easily tangled, end up laying on the floor getting contaminated and damaged. The probability of cables becoming tangled are not linearly correlated to cable length but rather exponentially correlated with cable length. In other words, longer cables are far more likely to get tangled. Because they are a nuisance to wind for storage, they are frequently left lying on the floor or draped over a gas machine. Long cables and hoses are also difficult to clean.

In some embodiments, the side of the module facing the patient includes a cable management system. In some embodiments the cable management system comprises an array of straps with snaps or Velcro fasteners to retain the individual cables and hoses. In some embodiments the cable management system comprises an array of hooks to retain the cables and hoses. Other cable and hose retention mechanisms are anticipated.

In some embodiments, the cable management system includes cables that are naturally coiled during the process of forming (e.g., molding) the outer insulation, somewhat like the traditional telephone cord. In some embodiments, the coils of cable or hoses may be much larger diameter than the traditional telephone cord. Coils that are 2-5 inches in diameter, much like a "slinky" may be preferable. Coils of larger diameter may have superior "memory" to retain the coiled shape. Electrical insulation materials such as urethane and nylon also provide superior "memory" characteristics compared to the PVC coating historically used on telephone cords.

These larger coils are easily stretched because the elongation is accomplished primarily by the lateral movement of adjacent coils, basically elongating the tubular shape, a movement that is minimally opposed by the "memory" of the molding process. This contrasts with an attempt to unwind each of the individual coils, a movement that is maximally opposed by the "memory" of the molding process. This is identical to the principals the make a "slinky" work; very easy to stretch in the direction of the coiled tube but nearly impossible to unwind an individual coil. The larger coils easily stretch laterally between the planes of each adjacent coil and stretch minimally in the plane of each coil.

In some embodiments, the coils of the cable management system are created by extrusion molding an electrically insulating plastic sheath over the wires of the cable. In some embodiments, the coils of the cable management system are created by extrusion molding a coil of plastic tubing and then inserting the wires of the cable into the tubing as a second operation.

Each piece of equipment on the surgical side of the anesthesia screen has traditionally been mounted on castor wheels and parked freestanding, somewhere on the floor surrounding the surgical table. In these locations, each of these pieces of equipment require a power cord or vacuum hose that lays on the floor and extends from the individual equipment to the wall plug or outlet. Additionally, each piece of equipment also has one or more cables and/or hoses that extend from the sterile surgical field, down to the floor, across the floor and are then plugged into the equipment. The freestanding equipment in the middle of the operating room floor is an obstruction to the movement of personnel, carts and gurneys. The cords, cables and hoses laying on the floor create a tripping hazard for operating room personnel, and also create an obstruction to rolling carts.

In some embodiments, the module can solve these problems, and other problems as well. In some embodiments, the module includes a lower section that can fit under the arm-board of the surgical table, utilizing the currently wasted space under the arm-board. In some embodiments, this lower section may have a larger footprint than the tower-like upper section that may be located against the anesthesia side of the arm-board. In some embodiments, a bulbous-shaped lower section creates much more space and volume for accommodating more pieces of electronic and electromechanical equipment—the added volume filling the unused volume under the arm-board.

In some embodiments, the bulbous lower section allows heavier equipment to be mounted down low in the module for added stability. In some embodiments, the larger footprint of the bulbous lower section allows a broader base for added stability. In some embodiments, it may be advantageous to mount heavier equipment near the rear of the module to balance the weight of the tower-like upper section that may be mounted over the front of the bulbous lower section. This prevents the tendency for the forward mounted tower to cause forward tipping. In some embodiments, the module may be suspended from the ceiling of the operating room on a "boom." Equipment suspended from ceiling mounted booms are well-known in the operating room.

In some embodiments, the rear side of the bulbous lower section may be positioned approximately in the same plane as the surgical drape hanging down from the surgical side of the arm-board. The surgical drape generally terminates 18-24 inches above the floor, allowing the rear of the bulbous lower section to be uniquely accessed from the surgical side of the anesthesia screen, below the lower edge of the surgical drape. In some embodiments, electrical plug-ins and hose connections for the various pieces of surgical equipment housed in the module may be located on the rear side of the bulbous lower section.

Alternately or in addition, in some embodiments, if the staff prefers to access cable and hose plug-ins at a higher, more convenient level, the cable and hose plug-ins may be positioned on the side of the module facing away from the patient or on the top surface of the lower section, near the side of the module facing away from the patient, since there is no surgical drape hanging down in this area.

In some embodiments, cables and hoses exiting the sterile surgical field may uniquely be dropped off of the sterile field adjacent the anesthesia screen. From this location, the cables and hoses drop nearly straight down to be attached to the cable and hose plug-ins on the rear the bulbous lower section or the side of the bulbous lower section facing away from the patient. In this unique location, there is no need for the cables and hoses to lay on the floor while traversing the distance to the equipment. In this unique location, there is no need for the cables and hoses to even touch the floor while traversing the distance to the equipment. This unique location next to the surgical drape and below the arm-board is the only place in the entire operating room where cables and hoses from supporting equipment can access the sterile surgical field without traversing or even touching the floor of the operating room and creating a tripping hazard for operating room personnel.

In some embodiments, consolidating the surgical equipment into the module also eliminates the obstructions caused by that equipment when it is free-standing in the middle of the operating room floor. It also eliminates the need for power cords and vacuum hoses traversing the floor to connect the equipment to the wall outlets.

Locating electrical and electromechanical equipment under the arm-board, necessarily subjects that equipment to a potential hazard from spilled water, spilled salt water (saline) and blood. In some embodiments, in order to protect this equipment from spilled fluids, the module is substantially covered in a water-resistant housing or "cowling."

For many decades, it has been an accepted axiom in the operating room; the air below the level of the surgical table is contaminated with skin cells (squames) and bacteria shed from the skin of the surgical personnel. These squames are shed from the skin of the operating room personnel into the air of the operating room. Once airborne, the squames are pushed toward the floor and vents near the floor, by the downward operating room ventilation airflow.

Waste heat from surgical equipment released near the floor, for example, heater-cooler units and forced-air warming units, has been proven to form into convection currents of rising warm air. When this waste heat is released near the floor, the rising convection currents can mobilize contaminates and bacteria that normally resident near or on the floor, up and into the sterile surgical field. If waste heat could be prevented from being within 4 feet of the floor where most of the airborne contaminates are concentrated, basically the height of the surgical table, it is believed that infections can be reduced.

The various pieces of electronic and electromechanical equipment housed within the module disclosed herein can produce relatively large amounts of waste heat. The bulbous lower section of the module is placed on the floor next to the surgical table and is below table height since it is under the arm-board. Releasing waste heat in this location on the floor next to the surgical table may cause a risk of sterile field contamination from the rising waste heat that may include squames and other contaminants. In some embodiments, the module may include a waste heat management system to safely dispose of the waste heat created by the electronic and electromechanical equipment housed within the module.

It would be difficult or even impossible to manage the uncontained waste heat produced by electronic and electromechanical equipment mounted on a simple open rack because it can escape in any direction. In some embodiments, the module of this invention has a "cowling" covering substantially the entire outer surface. The cowling not only protects the equipment from accidental fluid damage but also confines the waste heat from the electronic and electromechanical equipment mounted within the module, to the inside of the module and cowling. In some embodiments, the confined waste heat can then be safely managed.

In some embodiments, the cowling cover of the module can form or support a waste heat management system. In some embodiments, the module includes a tower-like upper section attached to the topside of the lower section. In some embodiments, the tower-like upper section extends substantially vertically from the top side, near the front of the lower section. In some embodiments, the tower-like upper section is used for mounting monitor screens and cable management retentions at an easily accessible and convenient height. In some embodiments, the top of the tower-like upper section, is 5 feet or more above the operating room floor. At this height, waste heat can be exhausted from vents near the top of the tower-like upper section is vented into the operating room, well above the height of most airborne contaminates. In contrast, if the waste heat vented low (<4 feet above the floor), it may mobilize airborne contaminants up and into the sterile field causing a significant infection risk.

In some embodiments, the cowling of the tower-like upper section serves as a chimney, containing the rising waste heat until it can be safely discharged from outlet vents located near the top of the tower. In this case, air may be allowed to enter the module through inlet vents in the lower section, the air gets heated by the electronic and electromechanical equipment in the module and then by natural convection, the heated air rises within the tower-like upper section and is discharged through outlet vents near the top. In some embodiments, a filter and fan may be added to the waste heat management system in order to filter the waste heated air before discharging it into the operating room, or to filter inlet air.

In some embodiments, the inlet vents for the cooling air may be located in the tower-like upper section, above the level of the airborne contamination. At this level, the inlet air is relatively pure and therefore there is no risk of contaminating the equipment housed within the module with contaminated air. In some embodiments, a duct may connect the inlet vent in the tower-like upper section to the equipment space in the lower section. The clean inlet air may be drawn into inlet vents mounted high on the upper section and then ducted down to the equipment that needs cooling and then ducted back up to the tower to be discharged at a safe height above the airborne contaminates. In some embodiments, ionized air filter plates may be included in the ducting to provide added filtration of the air without added resistance to the airflow.

In some embodiments, a waste air management system may be included in the module. In this case, the waste air management system may be designed to safely process and discharge waste air that may or may not contain waste heat. The waste air may be the by-product of equipment contained within the module or may be a waste product of other OR equipment, besides the monitors. An example of waste air producing equipment may include the smoke evacuation suction; used for evacuating electrosurgical smoke and filtering the smoke which has been shown to periodically contain virus particles.

Waste air producing equipment can also include operating room ventilation dead zone evacuation equipment; by vacuuming the air from the flow-boundary dead zones that naturally forms in front of the surgeons and anesthesia screen, the interference of the flow-boundary layers with the operating room ventilation can be reduced. This allows the ventilation airflow from the ceiling to reach the wound unimpeded by a flow-boundary dead zone. When ventilation airflow is kept moving, airborne contaminates in that air are kept airborne. As long as the airborne contaminates remain airborne, they do not land in the wound where they can cause an infection. When the ventilation airflow slows or even stops due to dead zone interference, gravity takes over and the airborne contaminates settle into the wound where they may cause infections. These dead zones of non-moving air that interfere with the operating room ventilation can be evacuated by placing vacuum hoses into the dead zone. The evacuated air can then be processed in order to safely discharge the air, back into the operating room. In some embodiments, the ventilation dead zone evacuation system may simultaneously serve as the surgical smoke evacuation suction. In this case the vacuum hose does not need to be attached to the electrosurgical pencil electrode, which many surgeons find to be cumbersome.

Waste air producing equipment can also include heater-cooler units (HCU) that produce contaminated waste heated air that needs to be processed and safely discharged. In this case, the waste heated air is a byproduct of cooling the refrigeration compressor of the HCU. Forced-air warming units (FAW) also produce contaminated waste heated air that needs to be processed and safely discharged. The FAW systems exhaust waste air from under the surgical drape where it escapes from under the surgical table near the floor. In some embodiments, this waste heated air can be contained and vacuumed up for safe disposal. Electrosurgical units and other surgical equipment also produce waste heated air that needs to be processed and safely discharged.

In some embodiments, the waste air management system may be used to evacuate and/or dilute the air under the surgical drape, especially near the patient's head, neck and chest. Alcohol from the surgical prep solution may pool under the drapes and then evaporate providing fuel for a fire. Waste oxygen from an unrestricted oxygen supplementation system such as nasal prongs may also pool under the drapes providing an oxidant for a fire. Then, add a spark from either the electro-cautery or a laser and highly dangerous operating room fires can occur. These fires occur far too frequently. Even the surgical drape can burn in the presence of an oxygen-enriched environment.

In some embodiments, it may be advantageous to remove the air and oxygen and alcohol vapors trapped under the surgical drape. In some embodiments, a vacuum hose may be placed near the shoulders, chest and neck of the patient. In some embodiments, the proximal end of the vacuum hose may plug into the inlet side of the waste air management system, for a convenient source of low velocity, low pressure vacuum.

In all of the instances, the waste heated air can be vacuumed, filtered and discharged at a height that does not allow any waste heat to mobilize contaminates normally resident near the floor, up and into the sterile field. In a possibly preferred embodiment, the air discharge can be at a height that is greater than 4 feet off of the floor.

In some embodiments, the waste air management system includes an air plenum containing an air filter. One or more air inlets allow waste air to enter the plenum from either the equipment housed in the module or from external equipment sources. A fan propels the waste air through the filter and exhausts the air from the plenum into a substantially vertical vent tube. In some embodiments, the substantially vertical vent tube extends upward to a height of more than 5 feet above the floor, before discharging the processed waste air from outlet vents near the top of the substantially vertical vent tube. In some embodiments, ultraviolet lights (UV) may be included in the plenum on one or both sides of the filter. In this location, the UV radiation can kill any living organisms that may have been captured by the filter. In some embodiments, a fabric sock-like filter may be attached to an outlet vent. The sock-like filter diffuses the air being discharged into the operating room to avoid jets and turbulent air currents. A sock-like filter also muffles the sound of the fan reducing the well-known OR noise created by various equipment cooling and smoke evacuation fans.

In some embodiments, the substantially vertical vent tube may be a rigid tube. In some embodiments, the substantially vertical vent tube may be the tower-like upper section of the module. In some embodiments, the substantially vertical vent tube is an inflatable, collapsible tube made of fabric, plastic film or fabric laminated to or coated with a plastic film. In some embodiments, the inflatable, collapsible tube may be disposable.

In some embodiments, the inflatable tube includes a substantially sealed distal end with one or more holes in the walls of the tube to allow the air to escape but create a flow obstruction causing the pressure within the inflatable tube to increase. The increased pressure in the inflatable tube causes the inflatable tube to assume an erect shape. In some embodiments, the erect inflatable tube extends substantially vertically, in order to terminate at a height of more than 5 feet above the floor. In some embodiments, the erect inflatable tube extends diagonally at an upward angle.

In some embodiments, it may be advantageous to dilute the air and oxygen and alcohol vapors trapped under the surgical drape with air. In some embodiments, an air hose may be placed near the shoulders, chest and neck of the patient. In some embodiments, a proximal end of the air hose may plug into a diversion from the discharge side of the waste air management system, for a convenient source of low velocity, positive pressure air.

In some embodiments, the output of the waste air management system may be diverted into a hose that may be hooked to an inflatable "hover" mattress for moving the patient off of the surgical table at the end of surgery. These "hover" mattresses are known in the arts and are inflated with pressurized air, which is released through holes on the bottom side of the mattress. The released air is effectively trapped under the mattress forming an air cushion on which the mattress and the patient effectively float, allowing the patient to be easily slid from the table to the gurney.

In some embodiments, the fan in the waste air management system also conveniently provides the pressurized air for a "hover" mattress. Air may be diverted from the outlet side of the waste air management system, into a hose that is attached to a "hover" mattress.

In some embodiments, the relocation module of the instant invention may also contain the components of the anesthesia gas machine. So-called "gas machines" are relatively simple assortments of piping, valves, flow meters, vaporizers and a ventilator. These could be located within the module or attached to the module for further consolidation of equipment and for improved access to the patient. The close proximity to the patient not only shortens the ventilation tubing but also shortens the sampling tubing for the carbon dioxide monitor. The close proximity of the anesthesia gas machine to the patient also allows continuous observation of the patient while adjusting the gas and anesthetic flows.

In some embodiments, the relocation module may include an air/oxygen blender to supply oxygen-enriched air to the patient for facemask and nasal prong delivery. This may be especially advantageous because of the very short distance between the module and the patient's head. Adding an air/oxygen blender may also be advantageous because many of the anesthesia machines do not include these devices. In some embodiments, the emergency oxygen, air and nitrous oxide tanks for the anesthesia machine may be mounted on the lower portion of the module in order to keep the center of gravity as low as possible. In some embodiments, it may be advantageous to mount these tanks horizontally on the sides or rear of the lower portion of the module rather than their traditional vertical mounting orientation, in order to avoid interfering with the arm board of the surgical table. In some embodiments, it may be advantageous to mount these tanks diagonally on the sides of the lower portion of the module rather than their traditional vertical mounting orientation, in order to avoid interfering with the arm board of the surgical table. In this case, a tank that is longer than the depth of the module can still be accommodated by locating the valve of the tank at the upper end of the diagonal near the front of the module. The closed end of the tank can thus be located at the lower end of the diagonal near the rear of the module where it fits nicely under the arm-board. In some embodiments, the oxygen, air and nitrous oxide hoses supplying the anesthesia machine may advantageously hang from the ceiling and connect to gas inlets in the top of the upper section of the module. In this location, the gas hoses are uniquely unobtrusive to the operating room staff.

In some embodiments, locating the anesthesia machine in or on the module allows direct access for and sensors and monitors related to the anesthesia machine, to input data to the electronic anesthetic record being recorded by equipment in the module.

In some embodiments, the shared fan, plenum, filter and discharge system of the waste air management system improves the efficiency, space requirements and cost in the operating room by consolidating multiple pieces of equipment into one. Currently, individual pieces of surgical equipment that produce waste air and waste heat are generally located on the floor, somewhere around the surgical table. This is exactly the worst place for this equipment to be located because the waste air and heat from this equipment is vented near the floor. The waste heat and air can then heat the contaminated air normally resident near the floor, and then carry contaminating particles and bacteria from the floor, up and into the sterile surgical field. Consolidating all the surgical support equipment in the bulbous lower section of the module with a single waste air management system eliminates waste air and heat from being vented near the floor, reducing the risk of airborne contamination.

Locating that single waste air management system in the bulbous lower section of the module and placing it under the arm-board of the surgical table totally removes it from all operating room traffic while providing the shortest possible hose distance to the patient, either on the surgical or anesthesia side of the anesthesia screen. Locating the waste air management system under the arm-board and surgical drape also minimizes and muffles the annoying fan noise.

Poor teamwork between anesthesia and surgery may be due to poor communication. For example, the anesthesia personnel may be experiencing problems maintaining normal vital signs and this may not be communicated quickly and clearly to the surgeon. "Yeah, the anesthesiologist mentioned his blood pressure was decreasing but I didn't realize it was to a critical level, so I went ahead and finished the procedure." A failure of the surgeon to understand the situation, can result in a wide variety of complications ranging in severity from mild to fatal. In some embodiments, a solution to this problem may be to mount a vital signs display screen on the rear of the tower-like upper section of the module, facing the surgeon. In this unique location viewable over the top of the anesthesia screen, the surgeon can be constantly aware of the patient's vital signs.

In some embodiments, the collection canisters for waste fluid and blood may be conveniently mounted on the module. Mounting the canisters on the module eliminates the need for vacuum tubing to lay on the floor while traversing from the wall outlet to the canister and from the surgical field to the canister. Optical or infrared fluid level sensors may be conveniently mounted in the module, adjacent the canister(s). In some embodiments, the fluid level monitors may automatically activate or deactivate the vacuum to a given canister, thereby automatically shifting the blood and fluid flow to a new canister as the previous one is filled.

In some embodiments, the controls and display screens for the surgical equipment housed in the module may be wirelessly connected to a portable display screen such as an iPad or "smart tablet," for convenient access by the nurse anywhere in the room. This allows the surgical nurse to monitor and control the equipment without walking across the room. This is convenient for the nurse and increases awareness of equipment conditions. Staff moving around the OR kick up contaminates from the floor into the air where they can be carried to the sterile surgical field by waste heat. A portable display screen minimizes surgical staff movement in the OR which has been shown to reduce airborne contamination and surgical site infections.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

In some embodiments, a module includes an equipment rack in a protective housing or "cowling." The module can be designed to advantageously fit into the unique location adjacent and/or under the arm-board of the surgical table-a location currently occupied by an IV pole on a rolling stand.

Figure 1:
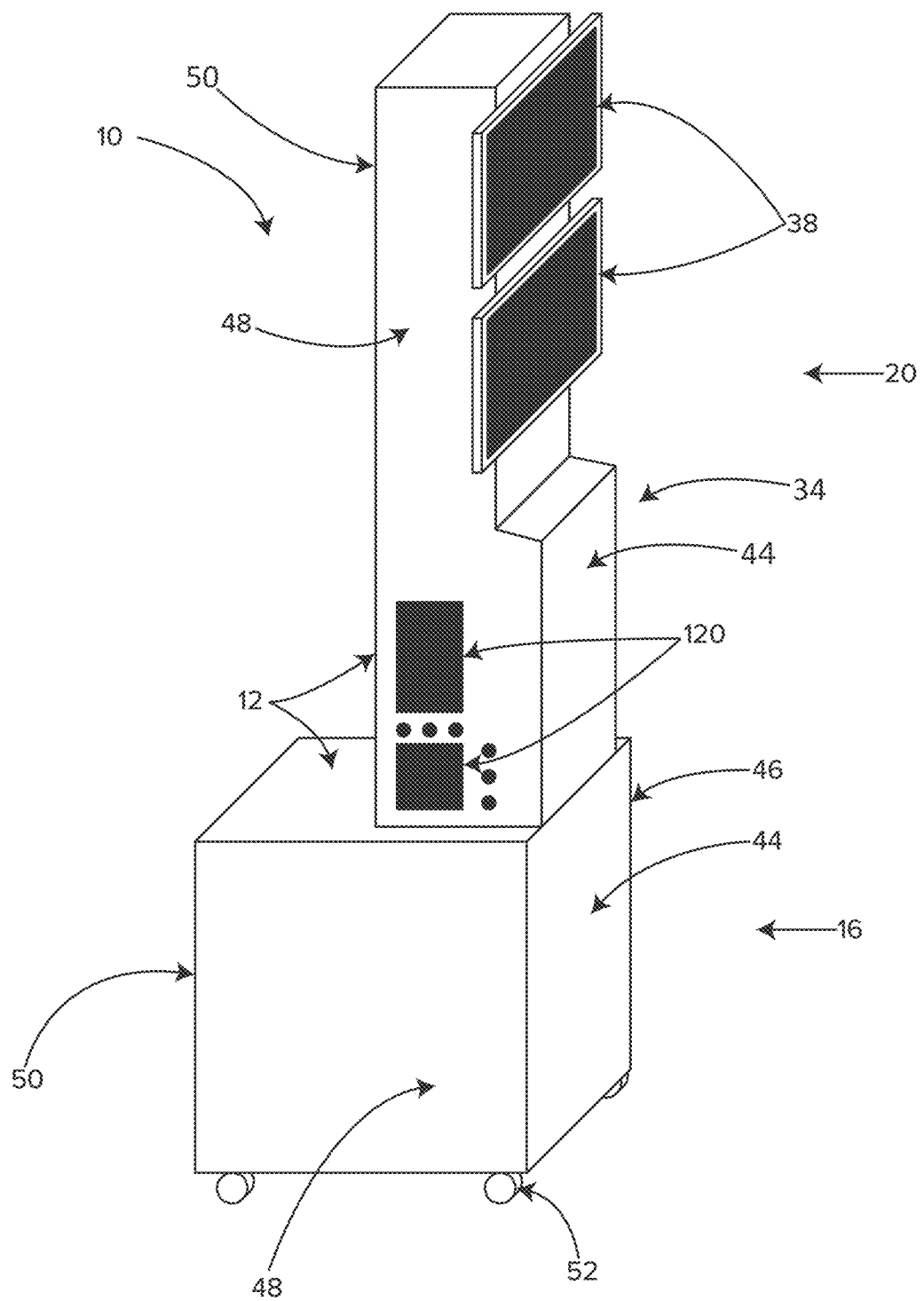
FIG. 1 shows a perspective view of an illustrative storage, airflow and cord management system, in accordance with at least one example.
Figure 2:
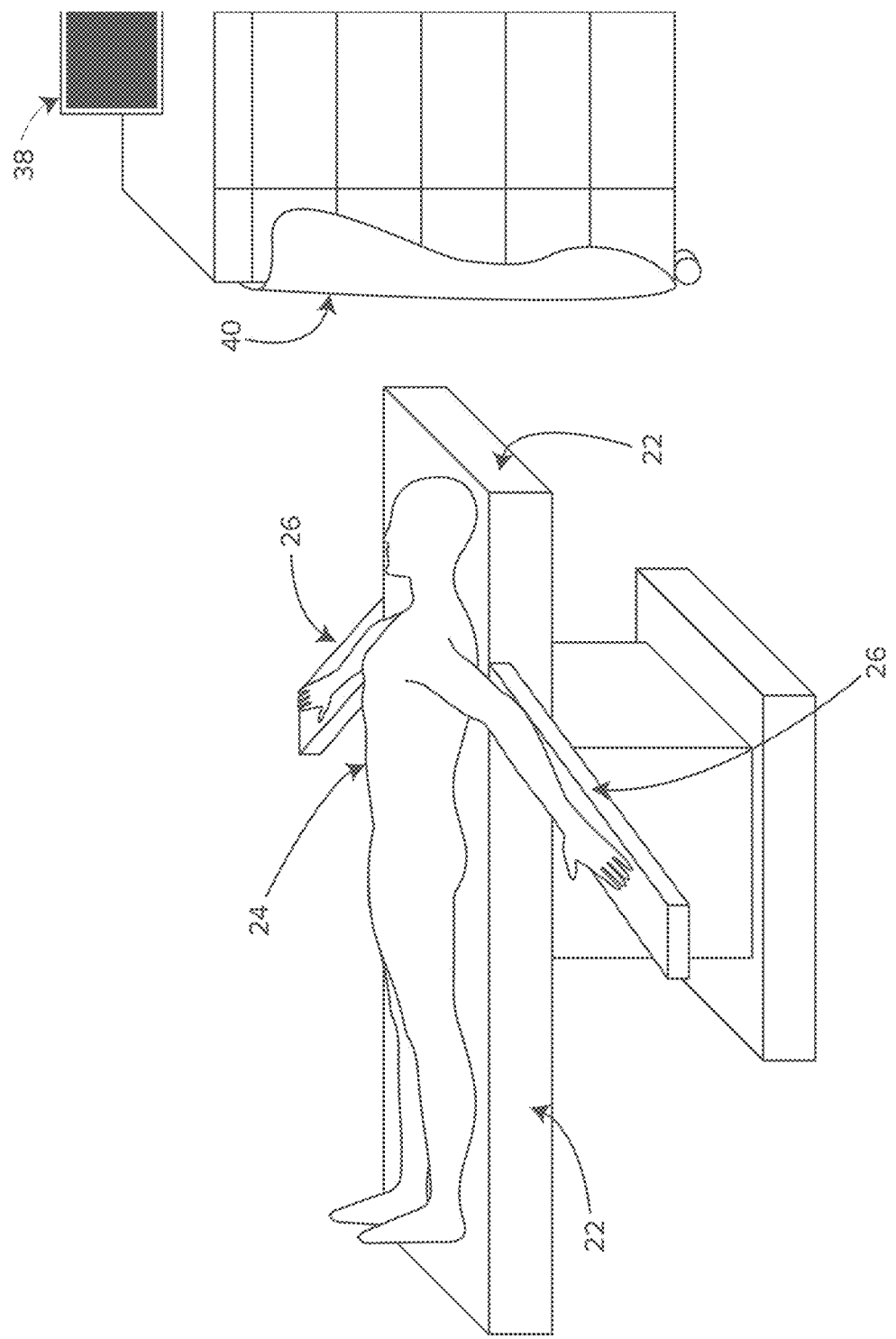
FIG. 2 shows a perspective view of an example standard operating room including a surgical table, and a patient laying on the table.

As shown in FIG. 2, the standard operating room includes a surgical table 22 on which the patient 24 is laying. Typically, the surgical table 22 includes arm-boards 26 that are attached to side rails of the table 22 and extend laterally from the table 22 at a slightly less than perpendicular angle. The patient's arms are rested on the arm-boards 26, which help to protect the arms from nerve damage and allow convenient access to the IV lines. This general configuration for surgery has evolved over the past century and is now a firmly embedded tradition.

Figure 3:
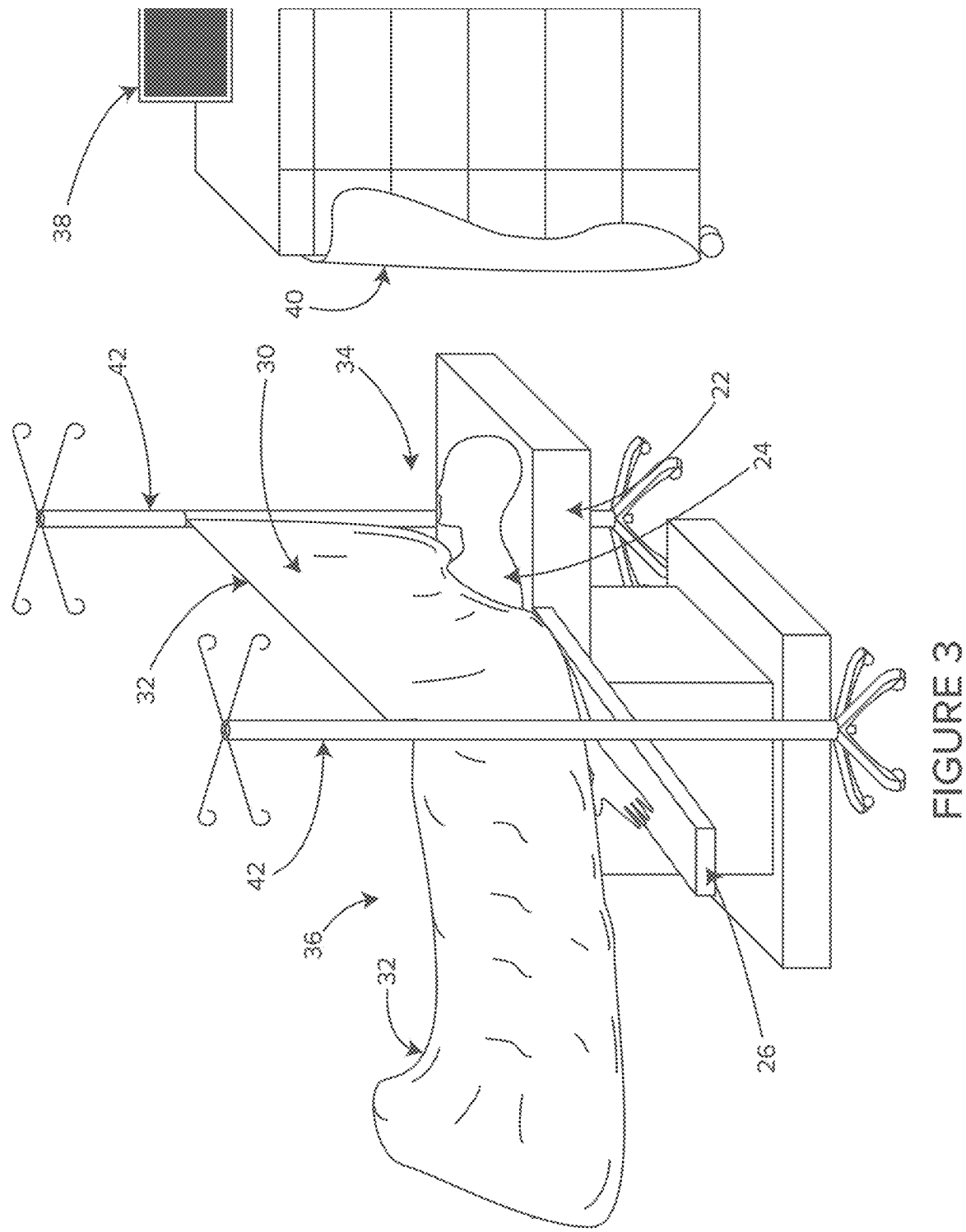
FIG. 3 shows a perspective view of the example standard operating room of FIG. 2, including two IV poles and a surgical drape.

As shown in FIG. 3, there are typically two IV poles 42 that are positioned adjacent the anesthesia side of the arm-boards 26, one on each side of the surgical table 22. Typically, the head end of the surgical drape 32 is elevated and attached between the two IV poles 42, creating a barrier between the surgical field and the anesthesia personnel who are located at the head end of the surgical table 22. This anesthesia screen 30 is a tradition that is meant to prevent skin contaminates shed from the anesthesia providers who are not wearing sterile gowns, from contaminating the sterile field.

The standard surgical draping shown in FIG. 3 naturally leads to surgery-related personnel and equipment being relegated to the surgical side 36 of the anesthesia screen 30. Further, the anesthesia-related personnel and equipment are naturally relegated to the anesthesia side 34 of the anesthesia screen 30.

Effectively, the anesthesia screen 30 and arm-boards 26 and the space under the arm-boards 26 have evolved into a "no-man's land" separating the surgical side 36 from the anesthesia side 34. Except for the IV pole 42 holding up the anesthesia screen 30, this "no-man's land" is totally wasted space in the modern operating room.

In some embodiments, the module 10 of this invention not only advantageously utilizes the currently wasted space under and adjacent the arm-board 26, but also capitalizes on the uniqueness of that wasted "no-man's land" floor space and the volume under the arm-board 26.

In some embodiments, the uniqueness of the space under and adjacent to the arm-board 26 includes but is not limited to the fact that it is less than 2 feet from the patient's head and less than 1 foot from the patient's arm. This is the only location in the operating room from which cables, wires, hoses and IV lines do not need to traverse a walkway or lay on the floor, in order to reach the patient 24.

As shown in FIGS. 2 and 3, an anesthesia gas machine 40 is typically located to the side of and slightly behind the anesthetist, who should be standing at the head end of the surgical table. Wires, cables and hoses originating from patient monitors 38 must necessarily traverse across the distance between the anesthesia gas machine 40 and the patient 24. The wires, cables and hoses connecting the patient monitors 38 to the patient 24 are generally 10-12 feet long. The wires, cables and hoses hang to the floor, then traverse the floor and then ascend to the patient 24 laying on the surgical table 22. It is axiomatic that 5-8 monitoring cables and hoses along with 2-6 electric patient warming cables (e.g., that are 12-15 feet long), can create a tangled mess laying on the floor.

The tangled mess of cables and hoses on the floor create not only considerable additional work for the OR staff requiring coiling and cleaning between cases, but also create a tripping hazard for the staff. Finally, cables and hoses laying on the floor of the OR are easily damaged by rolling carts and gurneys.

However, in the example systems described herein, the close proximity of the space adjacent the arm-board 26 is taken advantage of to provide for shorter monitoring, warming system and equipment cables and hoses. In some embodiments, this short distance to the patient eliminates the cables and hoses from even touching the floor, much less traversing the floor. In some embodiments, this is accomplished by relocating the patient monitors 38 into the module 10. In some embodiments, the monitor electronics may be located at a distance from the surgical table 22, perhaps on the anesthesia gas machine 40, with only the terminations of the patient monitor cables and hoses attached to module 10. In some embodiments, the cables may be connected to the monitors located a distance away from the surgical table 22, by wireless communications or by a trunk cable.

Figure 4:
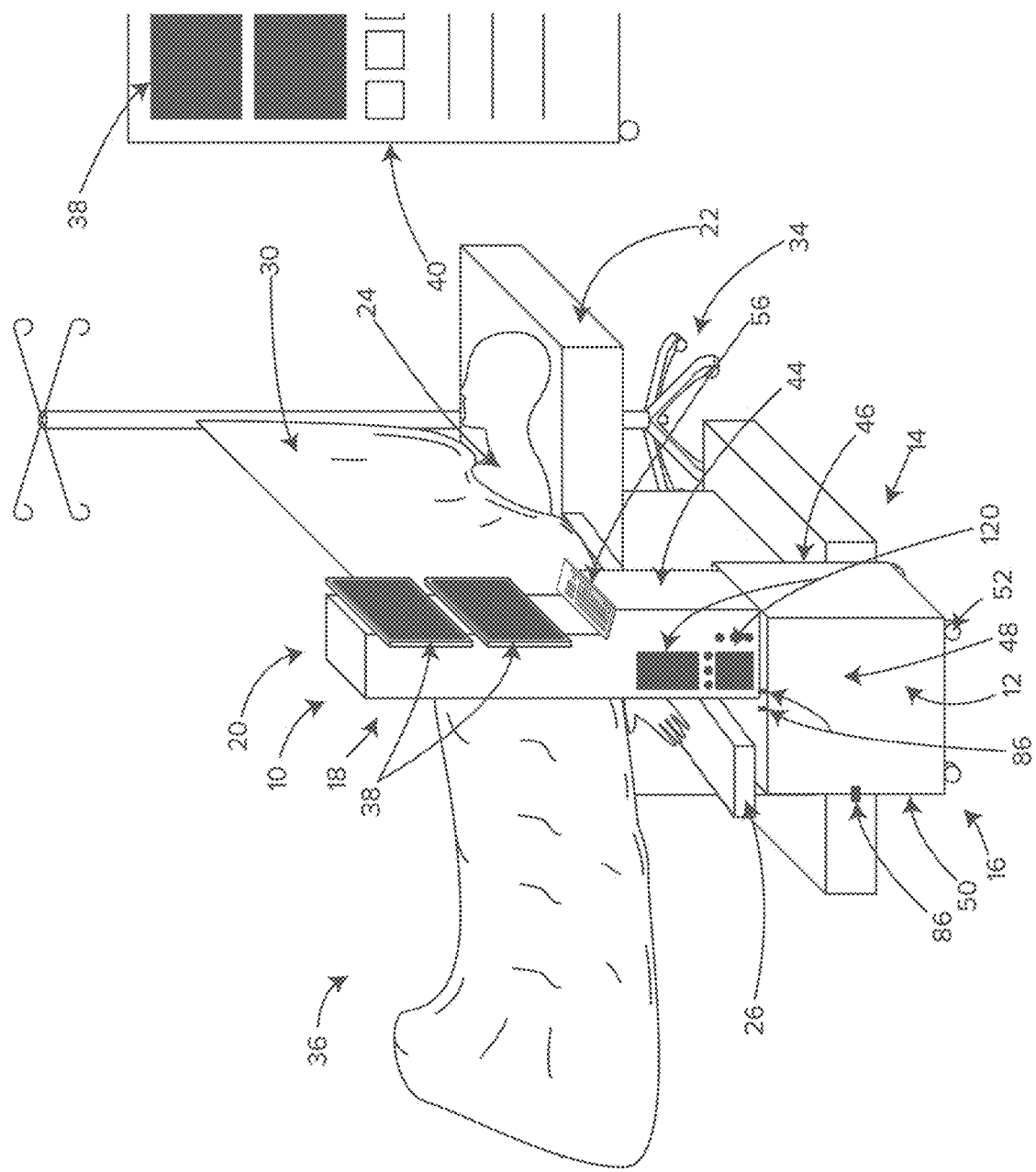
FIG. 4 shows a perspective view of the illustrative storage, airflow and cord management system of FIG. 1 in an operating room, in accordance with at least one example.

As shown in FIG. 4, in some embodiments, the uniqueness of the space under and adjacent to the arm-board 26 includes but is not limited to the fact that it is less than 2 feet from the patient's head and less than 1 foot from the patient's arm. Additionally, this is the only location in the operating room from which the patient monitoring display screens 38 can be viewed by the anesthetist in the same field of vision as the patient's head and the surgical field, while standing at the head end of the surgical table 22.

This location is in sharp contrast to the current location of patient monitoring display screens 38 mounted on the anesthesia gas machine 40 beside and behind the anesthetist. If the anesthetist is looking sideways at the monitors 38 located on the anesthesia machine 40, he or she is clearly not simultaneously observing the patient. Looking sideways at the monitors 38 located on the anesthesia machine 40 is a whole different field of vision-away from the patient, a distraction from the primary monitor: observation of the patient.

Currently, when the patient monitors audibly alarm, the anesthetist's attention is drawn away from the patient to the monitors, accentuating the distraction caused by the current location of the monitors on the anesthesia machine. In some embodiments, with the monitors, the patient and the surgical field to be observed by the anesthetist in a single field of vision, a light shining from that field of vision back toward the anesthetist may substitute for an audible alarm. Audible vital sign alarms for the patient monitors are not only distractions for the surgical staff but significantly add to the noise in the OR. In some embodiments, one or more relatively bright warning lights mounted on the tower or on one of the monitors that are mounted on the tower in this field of vision and aimed at the anesthetist, may be substituted for audible alarms.

In some embodiments, the light may advantageously be a directional LED that focuses its light in specific direction-toward the anesthesia provider. Mounting the one or more alarm lights on the patient monitor display that is adjustably mounted on the tower to provide the best viewing angle to the anesthetist, will automatically preferentially aim the alarm lights at the anesthetist. The lights may advantageously be red but other colors including white are anticipated. In some embodiments, the lights may be color coded, for example: patient monitor alarms may be red; IV infusion pump alarms may be orange; oxygen and ventilator alarms may be yellow; and miscellaneous non-critical equipment alarms such as warming blankets, may be blue.

In some embodiments, when the anesthetist acknowledges the alarm light by pressing a button (or functionally equivalent response), the light may decrease in intensity. In some embodiments, the light automatically turns off only when the alarm condition is resolved. In some embodiments, if the anesthetist fails to acknowledge the alarm light by pressing a button within a given amount of time, for example 20-30 seconds, a backup audible alarm may sound. In some embodiments, if the anesthetist acknowledges the alarm light by pressing a button (or functionally equivalent response) within a given amount of time, for example 20-30 seconds, the backup audible alarm may be muted so as not to distract the surgical staff and add to OR noise. In some embodiments, if the overhead lights in the OR have been dimmed, the alarm light may automatically decrease in intensity. In some embodiments, if the alarm condition is severe, the light may flash to increase noticeability.

The unique location of the tower on the module allows these one or more warning lights to be aimed away from the surgical field which is therefore not distracting to the surgeon. Only if the warning light is not noticed or ignored by the anesthetist, would a backup audible alarm which is distracting to the surgeon and OR staff be necessary.

In some embodiments, the patient monitors and monitor display screens 38 may be located on the module 10 next to the patient. In some embodiments, the patient monitor display screens 38 may be located on the module 10 next to the patient, while the monitor electronics may remain mounted to the anesthetic gas machine 40 or elsewhere. In this instance, the output of the patient monitors may be wirelessly transmitted to the patient monitor display screens 38 mounted on module 10, for convenient viewing.

As shown in FIG. 4, in some embodiments the rear side 50 of the module 10 is roughly in the same vertical plane as the surgical drape 32 hanging down from the arm-board 26, when the module 10 is located under the arm-board 26. In this unique location, wires, cables and hoses can exit the sterile surgical field adjacent the surgical side 36 of the anesthesia screen 30 and drop substantially downward to be plugged into electrical plug-ins and air inlet vents 86 located on the rear side 50 of the module 10. The wires, cables and hoses do not even have to touch the floor at that location. However, even if they do touch the floor, they do not cross any location where a surgeon would be standing nor do they cross any walking pathway. In this unique location adjacent the surgical side 36 of the arm-board 26, even wires, cables and hoses that are on the floor do not create a tripping hazard or an obstacle for small wheels. Locating module 10 adjacent to and under the arm-board 26, allows this unique and safe access for wires, cables and hoses from the sterile surgical field.

In some embodiments, it may be preferable to locate the wire and cable plug-ins and the hose inlet vents 86 on the side 48 of the module 10 facing away from the patient. On this side, the electrical plug-ins and hose inlet vents 86 can be located higher on the module 10 for more convenient access by staff. When the plug-ins and connectors are located on the side 48 of the module 10 facing away from the patient, it is more likely that the wires, cable and hoses may lay on the floor at the rear 50 of the module 10 and then rise to connect with the plug-ins and connectors. In contrast, wires, cables and hoses laying on the floor directly adjacent to the rear side 50 of the module 10, which is located under the arm-board 26 and surgical drape 32, will not create an obstacle for standing or walking.

The equipment location illustrated in FIG. 4 is unique in the entire operating room from the perspective of safe wire, cable and hose management, exiting the surgical field. All other locations for surgical support equipment require that wires, cables and hoses exit the surgical field and traverse the floor between the surgical table 22 and the equipment. As a result, this creates a tripping hazard for personnel and obstacle for small wheels.

In some embodiments, as shown in FIG. 4, the module 10 has 4 or more sides. When positioned in the unique "no-man's land" under and adjacent the arm-board 26, two of the sides 48 and 50 of module 10 are naturally available for surgical staff access and surgical equipment connections. In this position, two of the sides 44 and 46 of module 10 are naturally available for anesthesia staff access and anesthesia equipment connections. There is no other location in the operating room that can be advantageously "shared" by both anesthesia and surgery (two teams that do not historically share very well).

In some embodiments, the front face 44 of module 10 is substantially facing the anesthesia provider. Therefore, the front face 44 may naturally include controls and displays 38 for the anesthesia monitors and equipment. The front face 44 may also include plug-ins for certain equipment such as a heated clinician warming vest or specialty monitors. In some embodiments, the front face 44 includes a keyboard 56 and mouse pad for data entry. Other equipment such as IV bag pressurizers, IV pumps and drug infusion pumps may also be mounted on the front face 44 for convenient access by the anesthetist.

In some embodiments, the monitor screens 38 and/or keyboard 56 may be mounted on swiveling brackets that allow side-to-side and/or up and down adjustment for improved viewing angles. In some embodiments, the monitor screen 38 may be mounted on brackets that swing into a position even closer to the patient (lateral to the centered midpoint of the module 10). From this unique location, the anesthetist has a very clear view of the monitor displays 38 in the same field of vision as the patient's head and the surgical field. No other monitor display 38 mounting location in the operating room can provide this simultaneous visual access to both the monitors 38 and the patient 24. With the monitor screen "aiming" at the anesthetist, an alarm light attached to the monitor screen will also aim directly at the anesthetist, assuring that it will be noticed.

In some embodiments, the side 46 of the module 10 facing the patient 24, can advantageously be used for its close proximity to the patient 24. In some embodiments, wire, cable and hose management may be located on the side 46 facing the patient 24. Most of these cables and hoses are for anesthesia purposes, including but not limited to electronic patient monitors, end-tidal carbon dioxide sampling, automated blood pressure monitors, electrically heated blankets and mattresses and waste oxygen scavenging and dilution.

In some embodiments, cables and hoses for surgical equipment may be advantageously managed from the side 46 of the module 10 facing the patient 24. Examples include but are not limited to air mattresses, pressure sensing mats, sequential compression leggings, capacitive coupling electrosurgical grounding electrodes and RFID antennae for detecting retained surgical items.

In some embodiments, the rear side 50 of the module 10 is open to the surgical side 36 of the anesthesia screen 30, below the surgical drape 32 hanging down from the arm-board 26. From this location, the rear side 50 can be accessed directly for plugging in wires, cables and hoses exiting the sterile surgical field. However, the low height of the access, below the lower edge of the surgical drape, may be considered to be inconvenient.

In some embodiments, the side 48 of module 10 facing away from the patient 24 may be advantageously accessed by the surgical nurse without encroaching on the anesthetist, the anesthetist's space or the anesthesia side 34 of the anesthesia screen 30. In some embodiments, the side 48 facing away from the patient 24 may include the controls and display screens 120 for surgical equipment contained within the module 10. This surgical equipment includes but is not limited to: the electrosurgical unit, the air mattress, the pressure sensing mat, the smoke evacuation unit, the dead-zone evacuation system, blood and fluid suction and disposal, the sequential compression leggings and the RFID surgical sponge and instrument counting and detection system.

In some embodiments, most of the surgical support equipment may be incorporated into module 10, which allows the surgical nurse or technician to monitor and control all of this equipment from a single location—the side 48 of the module 10 facing away from the patient 24. The consolidated surgical equipment controls and displays 120 become very efficient for the nurse to monitor compared to having the equipment scattered all over the operating room. This is also far more likely that problems will be noticed early than if the individual pieces of equipment are scattered all over the operating room as is the current practice. Efficient monitoring also means that patient safety is improved. In some embodiments, the displays and controls 120 for the surgical equipment may be located on the front face 44 of the module 10, or another face of the module.

In some embodiments, the controls and display screens for the surgical equipment housed in the module 10 may be wirelessly connected to a portable display screen such as an iPad or "smart tablet," for convenient access by the nurse anywhere in the room. This allows the surgical nurse to monitor and control the equipment without walking across the room. Minimizing surgical staff movement in the OR has been shown to reduce airborne contamination and surgical site infections.

In this unique location adjacent the arm-board 26, the various sides 44, 46, 48, 50 of module 10 are naturally and advantageously adapted for different functions. The rear side 50 and the side 48 facing away from the patient can be adapted for surgical purposes. The front side 44 and the side 46 facing the patient can be adapted for anesthesia purposes. The only place that this unique combination could be achieved is in the currently unoccupied "no-man's land" between the anesthesia 34 and surgery sides 36 of the operating room—the anesthesia screen 30 and arm-board 26. The instant invention is uniquely adapted to advantageously fit this location.

As described herein, sides 44, 46, 48, 50 can be distinct sides as in the planar sides of a rectangular cuboid shape, or another cuboid shape having more than 4 sides.

However, in other embodiments the sides can refer to side portions of a curved or irregular shaped volume. In some examples, the sides can refer to an approximately 90 degree or quarter span of the volume that forms the module 10.

In some embodiments, as shown in FIGS. 4-7, the module 10 includes a lower section 14 and an upper section 18. In general, the lower section 14 may contain the heavier equipment such as power supplies, the electro-surgical unit and monitor electronics. In general, the upper section 18 may contain lighter equipment and components such as ducting, fans, filters, cable management systems, wiring harnesses and monitoring screens 38. Keeping the heavy equipment in the lower section 14 improves the stability and reduces the risk of tipping.

Figure 5:
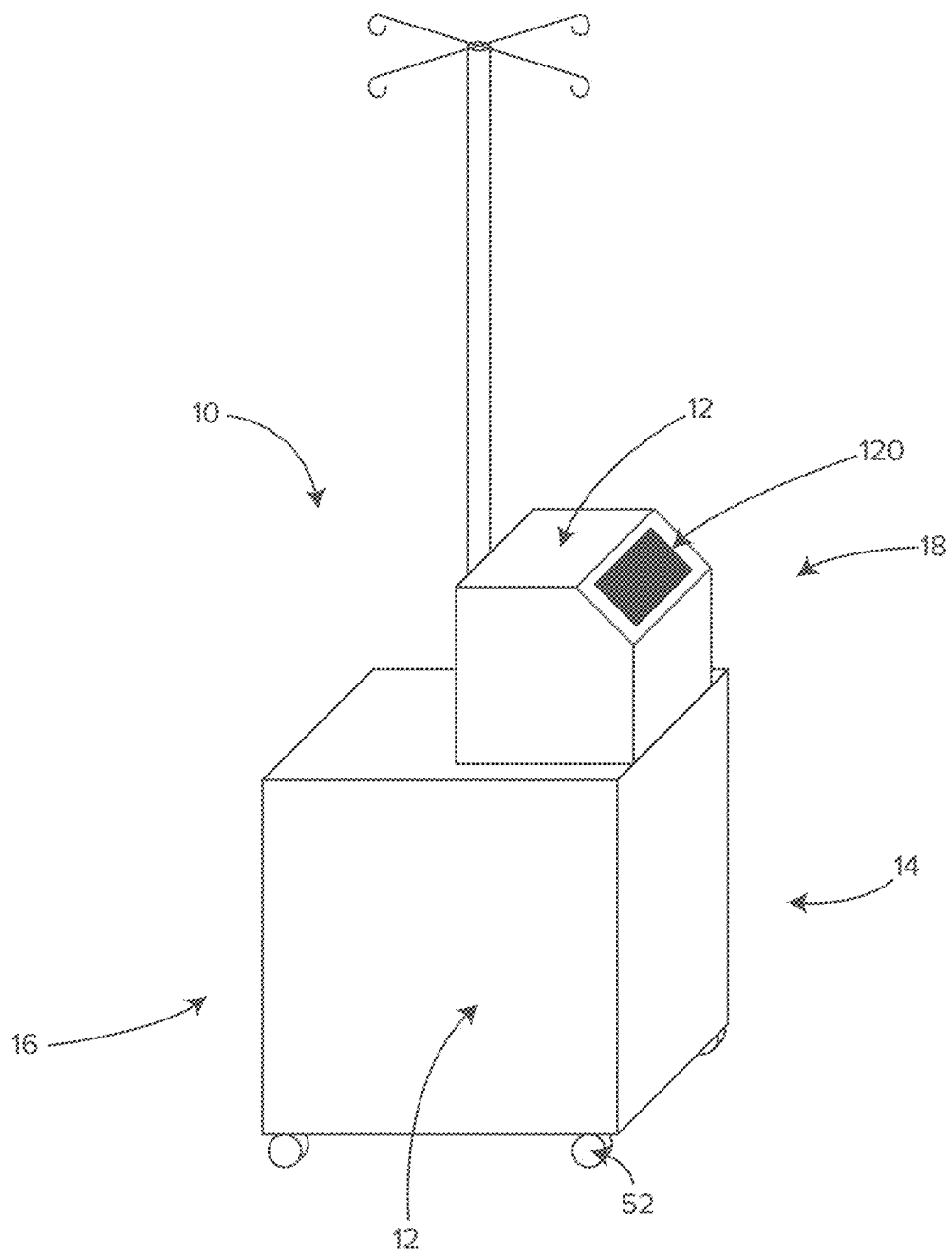
FIG. 5 shows a perspective view of another example of an illustrative storage, airflow and cord management system, in accordance with at least one example.
Figure 6:
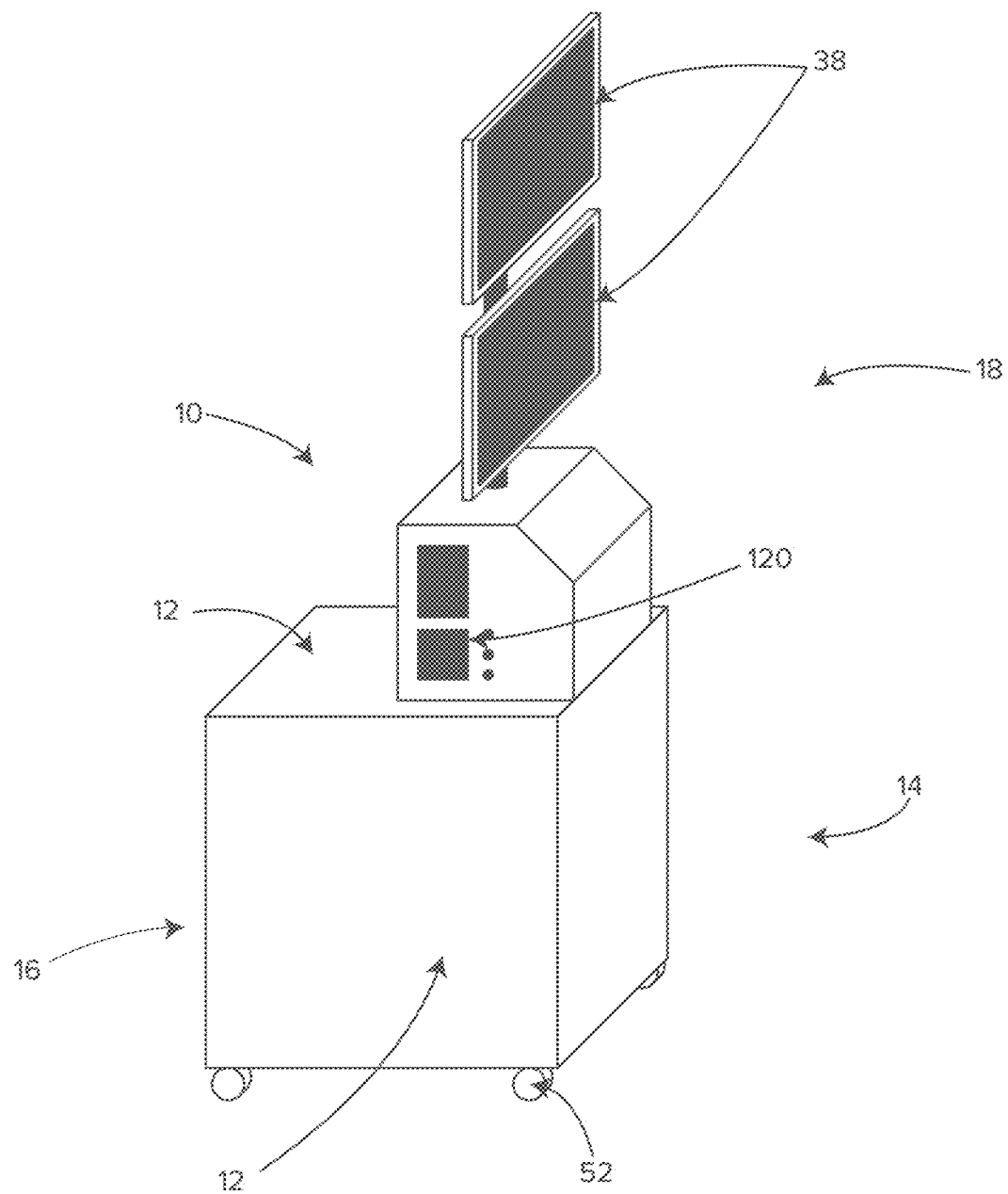
FIG. 6 shows a perspective view of another example of an illustrative storage, airflow and cord management system, in accordance with at least one example.

In some embodiments, as shown in FIGS. 4-6, the lower section 14 could be called a bulbous lower section 16. "Bulbous" is compared to the upper section 18. There are several advantages for the lower section 16 being "bulbous." The bulbous lower section 16 has an increased internal volume that can house much more equipment. The bulbous lower section 16 efficiently utilizes the otherwise wasted space under the arm-board 26. The bulbous lower section 16 substantially increases the footprint of the base of module 10, allowing the rear wheels to be much further to the rear of the module, substantially increasing the stability of the module 10. Heavier equipment may be located toward the rear of the bulbous lower section 16, which further increases the stability and lessens the likelihood of module 10 tipping forward.

In some embodiments, the bulbous lower section 16 may be of any size. In some embodiments, a cube roughly 24 inches on each side can fit under the arm-board 26. Other sizes and shapes are anticipated. A 24 inch cube may appear to be rather large and cumbersome but it is worth noting that the standard 5-wheeled base for an IV pole 42 is an area roughly 24 inches in diameter. Therefore, the floor occupied by and the traffic patterns affected by the 24 inch square of the bulbous lower section 16, is virtually identical to the 24 inch diameter circle of the current IV pole 42 that can sometimes be located in that same position. However, the volume above an IV pole base is wasted in contrast to the bulbous lower section 16 which may include 8 cubic feet or more, of volume that can house various surgical and anesthetic equipment. The bulbous lower section 16 very efficiently utilizes otherwise wasted volume under and adjacent to the arm-board 26. In some embodiments the bulbous lower section may include between 4 and 12 cubic feet of volume. In a possibly more preferred example, the bulbous lower section may include between 6 and 10 cubic feet of volume.

Figure 7:
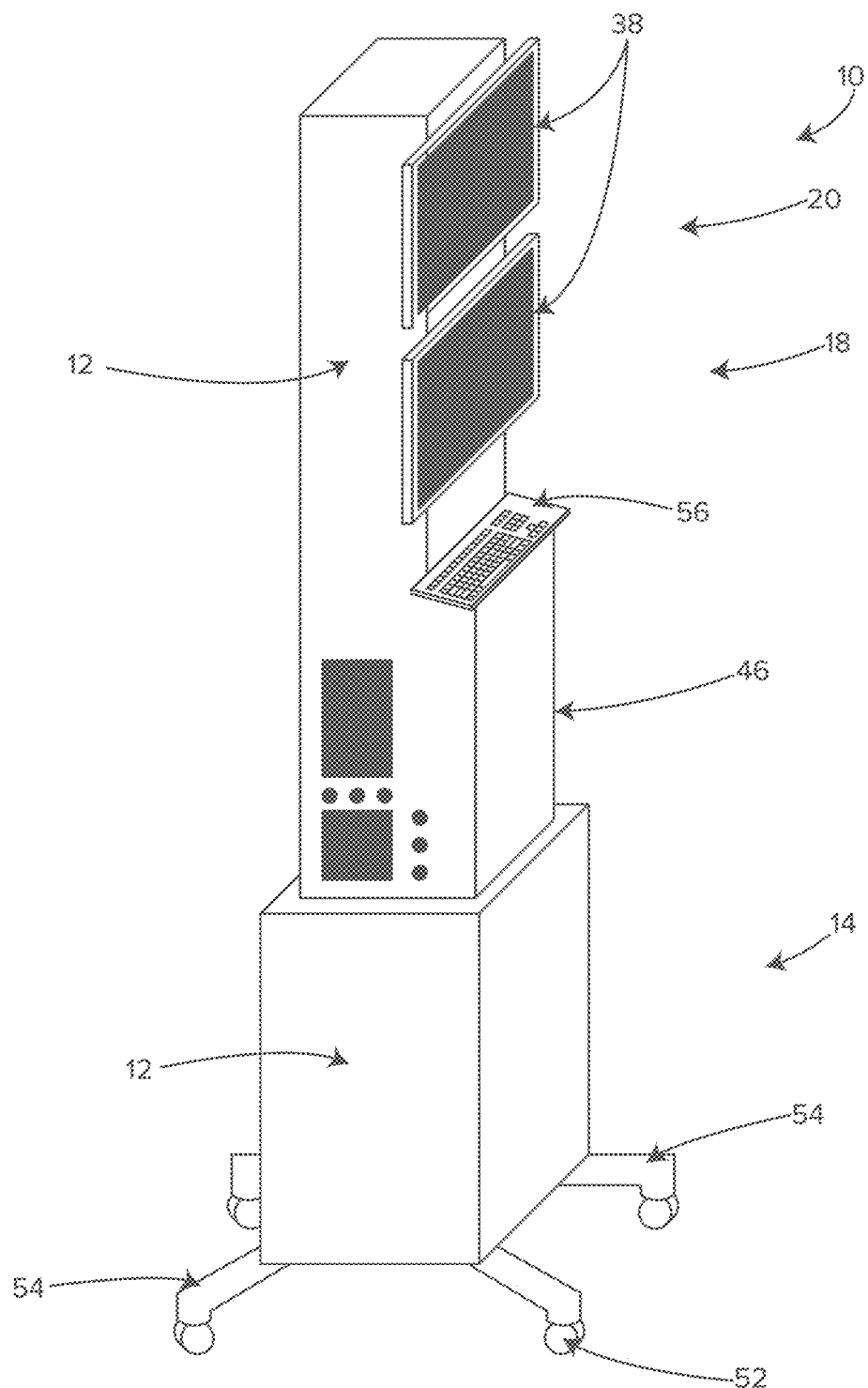
FIG. 7 shows a perspective view of another example of an illustrative storage, airflow and cord management system, in accordance with at least one example.

In some embodiments, as shown in FIG. 7, the lower section 14 may not be bulbous. In some embodiments, the lower section 14 may be designed to fit adjacent the arm-board 26 but may not go under the arm-board 26. In some embodiments, the lower section 14 may fit minimally under the arm-board 26. In this instance, the space under the arm-board 26 may be utilized for stability by adding short legs 54 extending rearward to mount castor wheels further rearward. Even if the volume under the arm-board 26 is not utilized for equipment storage, the volume adjacent the arm-board 26 may be efficiently utilized for storing equipment in the lower section 14 of the module 10.

In some embodiments, the module 10 of this invention has a shell or "cowling" 12 covering substantially the entire outer surface. Open equipment racks with like pieces of equipment stacked on their shelves that remain open and exposed must need to be kept at a safe distance from the surgical table 22. In contrast, creating an enclosed module 10 for storing various unrelated pieces of equipment is unique in the operating room. Creating an enclosed module 10 for storing various unrelated pieces of equipment makes it possible to place the module 10 near the surgical table 22 during a surgery. The cowling 12 can protect the equipment in the module 10 from accidental fluid damage by IV fluids, irrigation fluids and blood. Any open rack adjacent and under the arm-board 26, will be at high risk for damage from water, salt water and blood in this hazardous environment.

In some embodiments, the cowling 12 of module 10 is made of molded plastic, 3-D printed plastic, fiberglass, aluminum, steel or other suitable materials. The cowling is preferably fluid resistant if not fluid proof. The cowling 12 is preferably shaped so that water naturally runs off of it and that it has smooth surfaces for easy cleaning. Preferably any air inlet vents include overhangs that protect them from fluid ingress from spilled fluids. The access ports of the cowling 12 are preferably sealed when closed, to prevent fluid ingress.

In some embodiments, the cowling 12 of module 10 confines the waste heat from the electronic and electromechanical equipment mounted within the module 10, to the inside of the module 10 and cowling 12. In some embodiments, the confined waste heat can then be safely managed. It would be difficult or even impossible to manage the unconfined waste heat produced by electronic and electromechanical equipment mounted on a simple open rack or free-standing in the middle of the operating room floor.

In some embodiments, the cowling cover of the module 10 described herein contributes to a waste heat management system. The cowling 12 can substantially seal in the waste heat and control the discharge of the waste heat to exit at a predetermined location, such as an outlet vent. In some embodiments as shown at least in FIGS. 1, 4 and 7-12, the module 10 includes a tower-like upper section 20 attached to the topside of the lower section 14. In some embodiments, the tower-like upper section 20 extends substantially vertically from the topside, near the front of the lower section 14. In some embodiments, the cowling 12 of the tower-like upper section 20 serves as a chimney, containing the rising waste heat until it can be safely discharged from outlet vents located near the top of the tower.

In some embodiments, the top of the tower-like upper section 20 is 5 feet or more above the operating room floor. At this height, waste heat exhausted from vents near the top of the tower-like upper section 20 is vented into the operating room well above the height of most airborne contaminates. In some embodiments, air is allowed to enter the module 10 through inlet vents in the lower section 14, the air gets heated by the electronic and electromechanical equipment in the module 10 and then by natural convection, the heated air may rise within the tower-like upper section 20 and be discharged through outlet vents near the top of module 10.

In some embodiments, the air discharge can occur at a height between 3 and 15 feet above the floor that the module 10 is configured to rest on. In a preferred example, the air discharge can occur at a height of at least 4 feet off the floor. In a more preferred embodiment, the air discharge can occur at a height of at least 5 feet off the floor. In some embodiments, the air discharge can be connected to a venting system which removes the discharged air from the OR.

In some embodiments, a filter and fan may be added to the waste heat management system in order to filter the waste heated air before discharging it into the operating room, or to filter inlet air. The resistance to airflow caused by adding a filter to the airflow path may necessitate adding a fan to the waste heat management system. In some embodiments, a sock-like filter may be added to the outlet vent in order to diffuse the outlet air and muffle any fan noise.

In some embodiments, the inlet vents for the cooling air may be located in the tower-like upper section 20, four or more feet above the floor, above the level of the airborne contamination. At this level, the inlet air is relatively pure and therefore there is no risk of contaminated air causing contamination of the equipment housed within the module 10. In some embodiments, a duct may connect the inlet vent in the tower-like upper section 20 to the equipment space in the lower section 14. The clean inlet air can be drawn into inlet vents mounted high on the upper section 18 and then ducted down to the equipment that needs cooling and then ducted back up to the tower 20 to be discharged at a safe height above the airborne contaminates. In some embodiments, ionized air filter plates may be included in the ducting to provide added filtration of the air without added resistance to the airflow.

In some embodiments, the lower section 14 includes castor wheels 52. The castor wheels 52 may be located substantially in the four corners of the lower section 14. In some embodiments, the lower section may include more than 4 castor wheels. In some embodiments, and as shown in FIG. 7, the lower section 14 may include short "legs" 54 that stick 2-10 inches out from the perimeter of the base of the lower section 14. Castor wheels 52 may be attached near the distal ends of these short legs 54 to improve the stability of the module 10.

In some embodiments, the module 10 does not have wheels but is rather mounted to a movable boom hanging from the ceiling of the operating room. The boom can include two or more arms that articulate and are attached to a pivot point on the ceiling. This configuration allows the module 10 which is attached to the end of the boom, to be moved into a position adjacent the arm-board 26 and then moved away from that position, if for example a gurney needs to be placed against the side of the surgical table. In some embodiments, even the boom-mounted modules 10 advantageously include bulbous lower sections 16 to maximally capitalize on the wasted volume under the arm-board 26. In some embodiments, booms from the ceiling may advantageously include power cords, communication cables, air, oxygen and vacuum hoses that conveniently connect outlets in the ceiling to the module 10.

In some embodiments, the module 10 includes an upper section 18 as shown in FIGS. 4-7. In general, the upper section 18 is for housing or mounting lighter equipment and locating controls 120 and monitor displays 38 at a height where they can be conveniently accessed. In some embodiments, the upper section 18 may be a tower-like upper section 20 as shown in FIGS. 4 and 7. In this instance the top of the tower-like upper section 20 may be more than 4 feet above the floor. In some embodiments, the top of the tower-like upper section 20 may advantageously be 6 feet or more above the floor.

Using the example modules 10 described herein, heat and air can be more safely discharged at higher heights in the operating room because they cannot mobilize contaminates that normally reside near the floor. Therefore, a taller tower-like upper section 20 may advantageous.

In some embodiments, a patient monitor display screen 38 may be mounted on the rear of the tower-like upper section 20 of the module 10, facing the surgeon. In this unique location, viewable over the top of the anesthesia screen 30, the surgeon 108 can be constantly aware of the patient's vital signs.

In some embodiments, the upper section 18 of module 10 may be a medium height, for example 3-4 feet above the floor as shown in FIG. 6. In some embodiments, the upper section may be a relatively low height of 2-3 feet above the floor as shown in FIG. 5. In each case, the upper section 18 places the controls 120 and monitor displays 38 for the equipment enclosed in module 10, at a more convenient height for the operator.

In some embodiments, patient monitor display screens 38 may be mounted on one or more sides (e.g., faces, side portions) of the upper section 18 of module 10 as shown in FIGS. 4 and 7. In some embodiments, the patient monitor display screens 38 may be mounted on arms that attach to the top of the upper section 18 as shown in FIG. 6. In some embodiments, a keyboard 56 and/or mouse pad may also be mounted to the upper section 18 of module 10.

In some embodiments, upper section 18 includes a side 46 facing the patient. In some embodiments, if the upper section 18 is tower-like, the side 46 facing the patient is a relatively large surface area. For example, the side 46 facing the patient may be 12 inches wide (or more) and 48 inches tall (or more) which results in 4 square feet of surface area on the side 46 of the upper section 18. This large surface near the patient and facing the patient is uniquely located and sized for a cable and hose management system 58.

Figure 8:
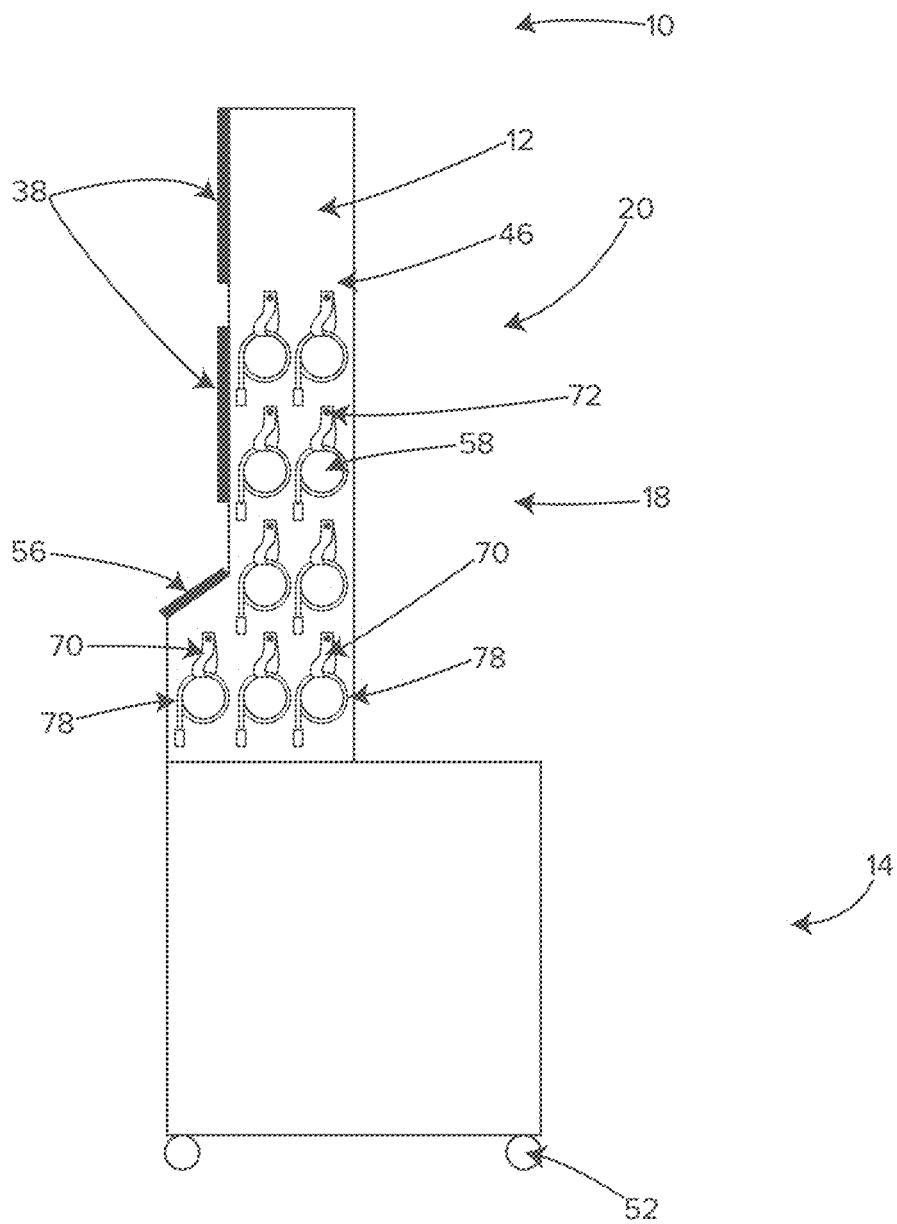
FIG. 8 shows a side view of an illustrative example of a cable and hose management system of the illustrative system of FIG. 7, in accordance with at least one example.

In some embodiments as shown in FIG. 8, the cable and hose management system 58 may comprise one or more straps 70 mounted on the side 46 facing the patient (e.g., configured to face the patient, configured to face the surgical table). In some embodiments, there may be an array of 8-15 straps 70. Each strap 70 may retain an individual cable or hose. These straps 70 may include a snap, Velcro or other closures means 72 in order to create an openable loop that can retain a coiled cable or hose.

Figure 9:
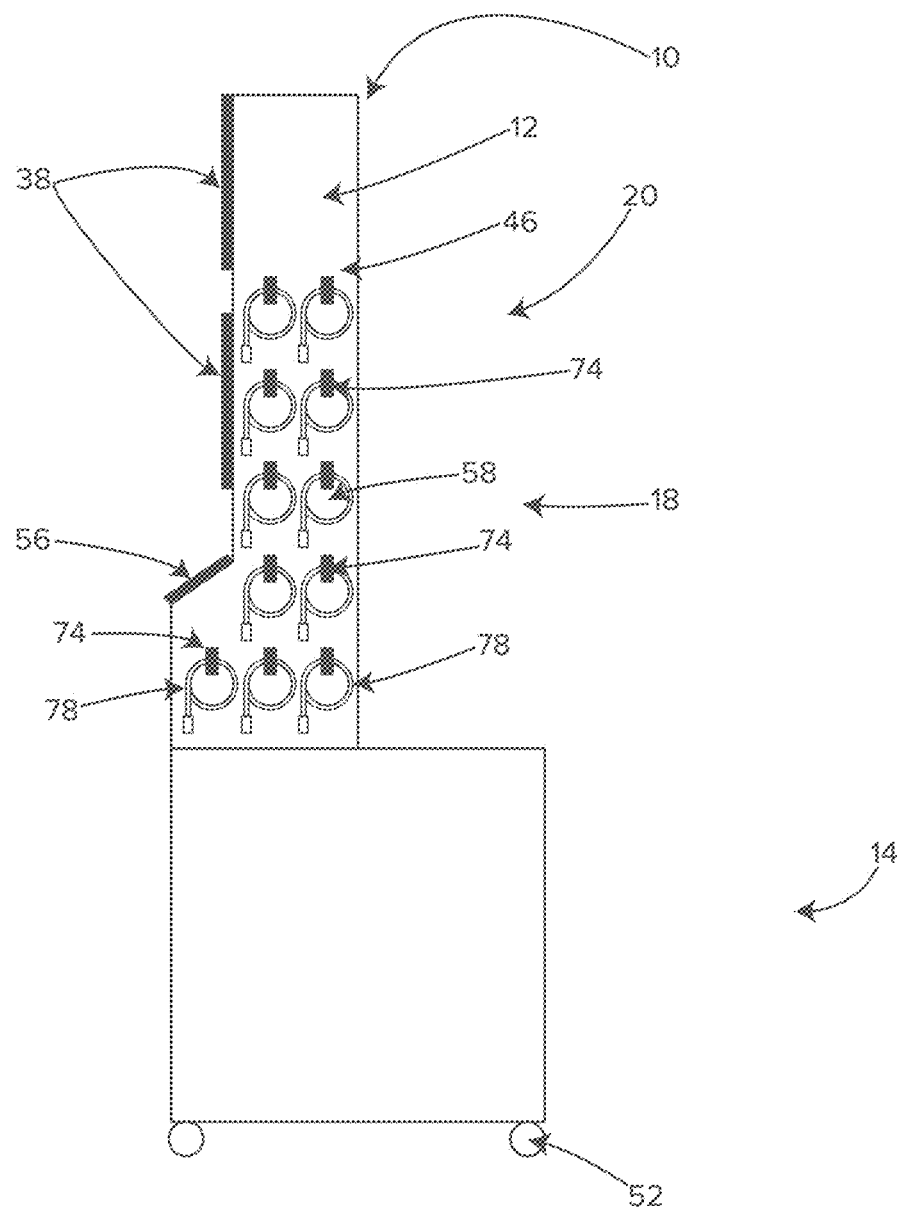
FIG. 9 shows a side view of another illustrative example of a cable and hose management system of the illustrative system of FIG. 7, in accordance with at least one example.

In some embodiments as shown in FIG. 9, the cable and hose management system 58 may comprise one or more hooks 74 mounted on the side 46 facing the patient. In some embodiments, there may be an array of 8-15 hooks 74. Each hook 74 may retain an individual cable or hose.

Figure 10:
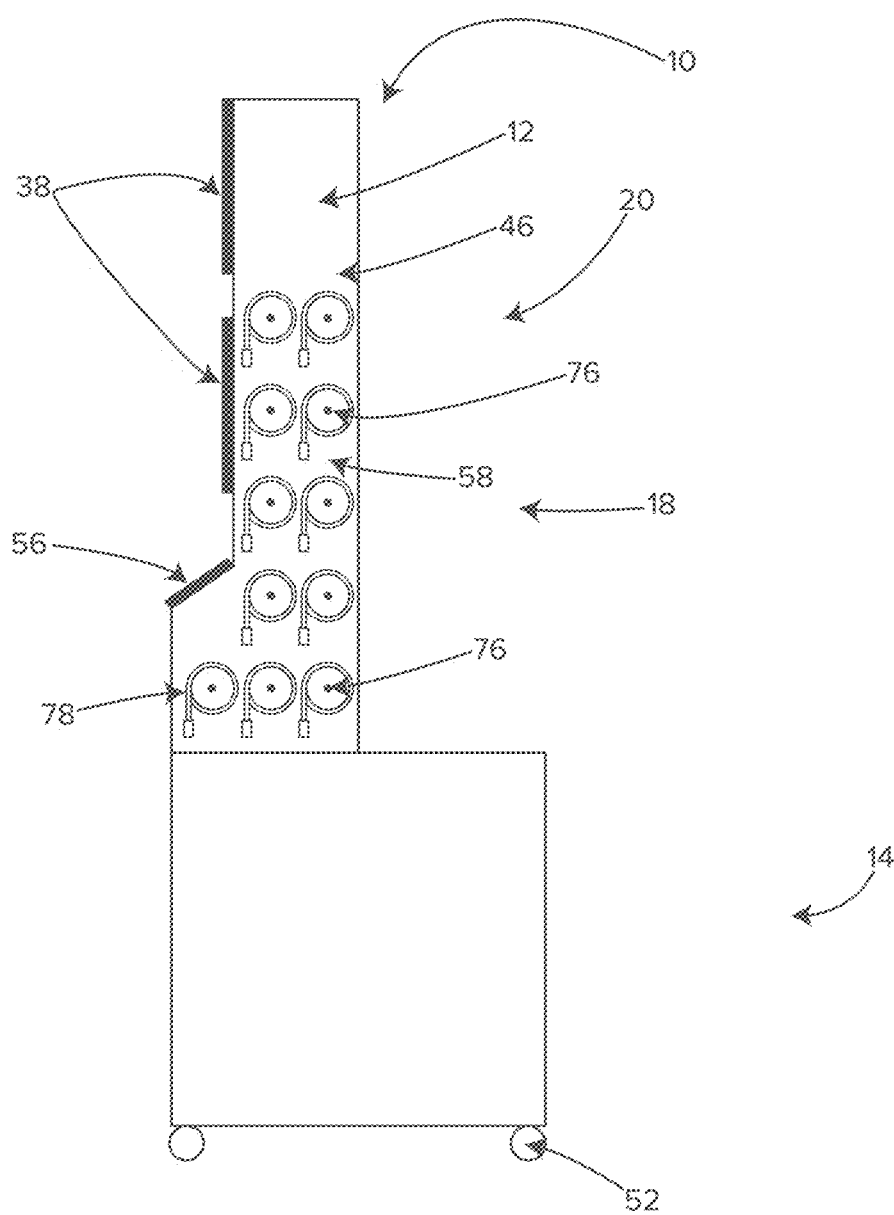
FIG. 10 shows a side view of another illustrative example of a cable and hose management system of the illustrative system of FIG. 7, in accordance with at least one example.

In some embodiments as shown in FIG. 10, the cable and hose management system 58 may comprise one or more reels 76 mounted on the side 46 facing the patient. In some embodiments, there may be an array of 8-15 reels 76. Each reel 76 may retain an individual cable or hose. These reels 76 may be used to wind the cables and hoses on to a spool for secure storage. The reels 76 may be manually operated, spring powered or powered by electric motors.

Figure 11:
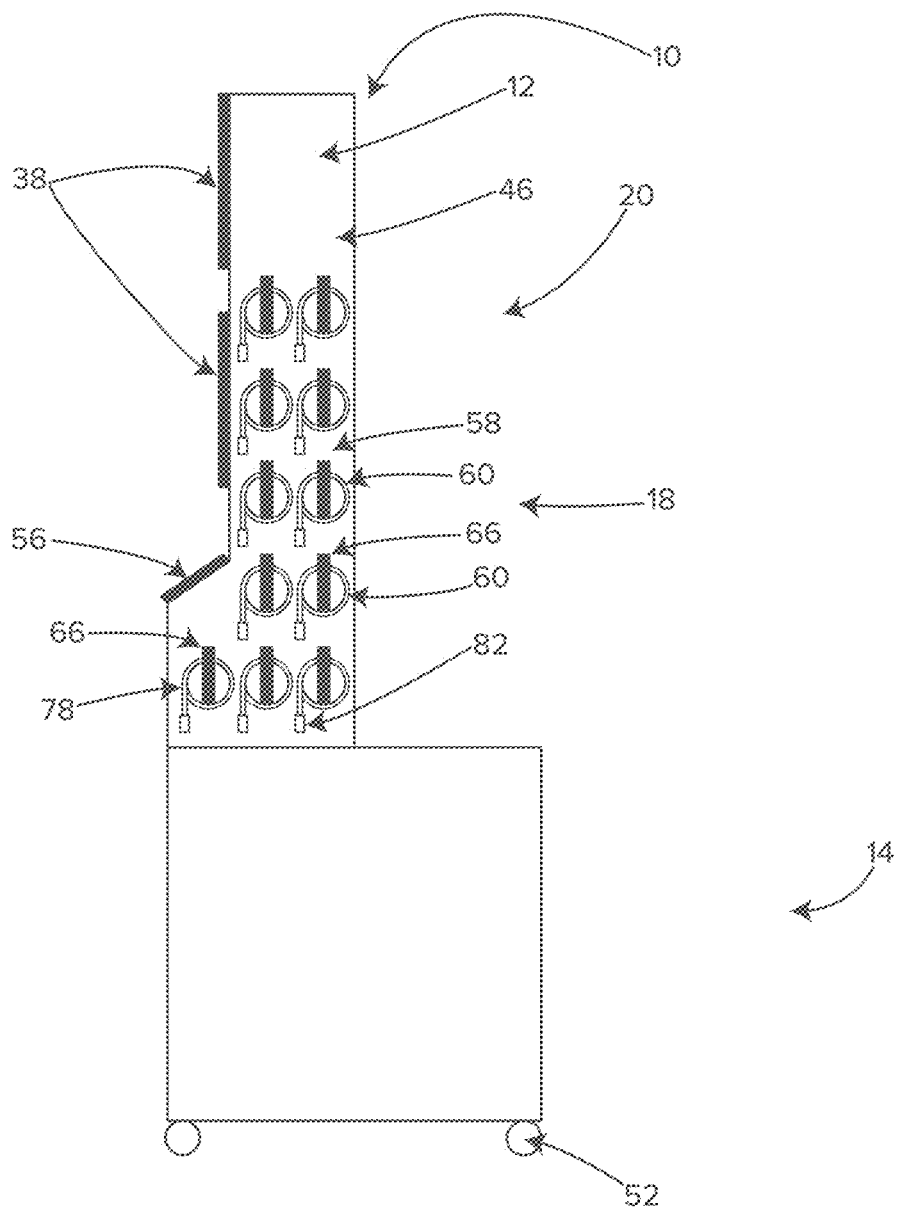
FIG. 11 shows a side view of another illustrative example of a cable and hose management system of the illustrative system of FIG. 7, in accordance with at least one example.
Figure 12:
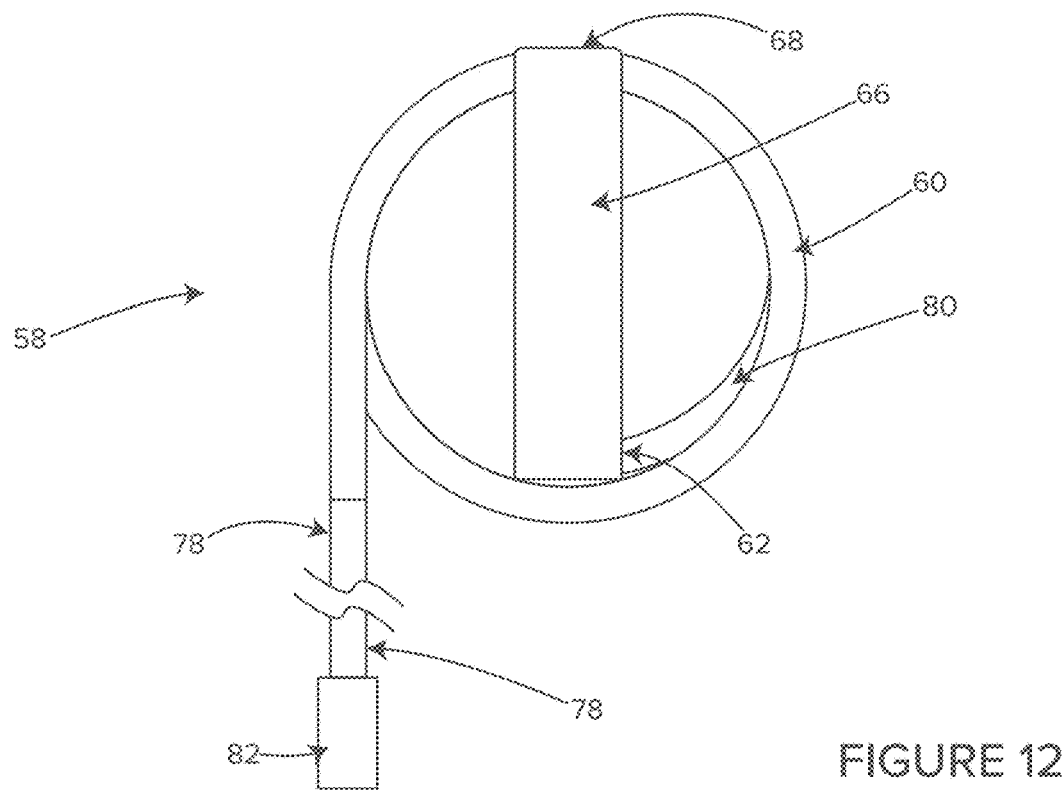
FIG. 12 shows a side view of an illustrative individual cable and hose management system of FIG. 10, in accordance with at least one example.
Figure 13:
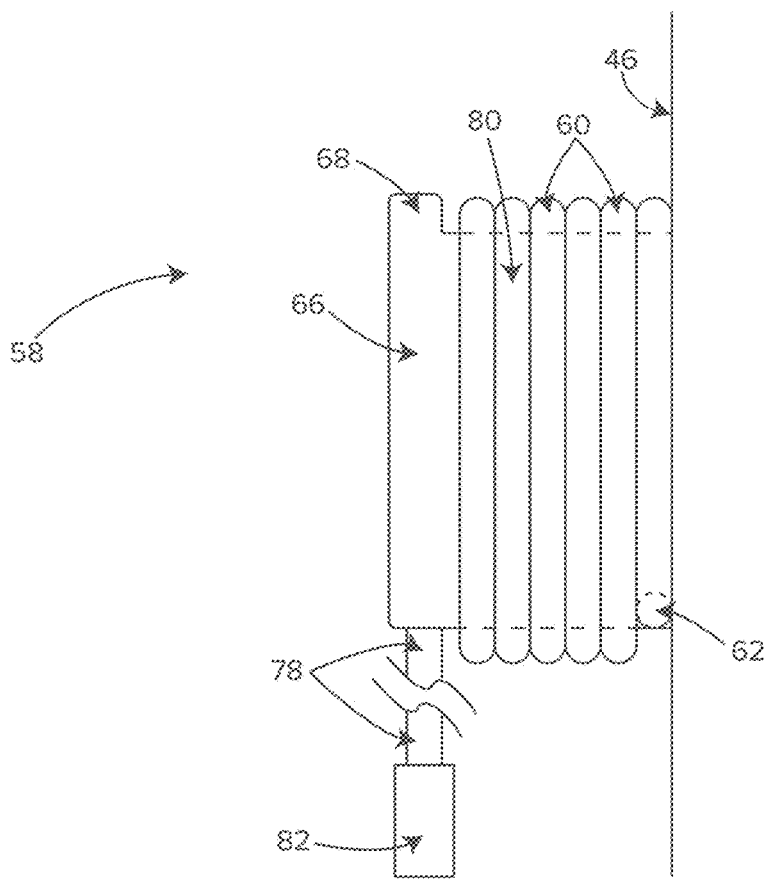
FIG. 13 shows a rear view of an illustrative cord of the cable and hose management system of FIG. 10, in accordance with at least one example.

In some embodiments as shown in FIG. 11, the cable management system comprises cables that are naturally coiled during the molding process of the outer insulation, somewhat like the traditional telephone cord. In some embodiments, the coils 60 of cable or hose may be much larger than the traditional telephone cord. As shown in FIGS. 12 and 13, coils 60 that are 2-5 inches in diameter, much like a "slinky" may be preferable. Coils 60 of larger diameter may have superior "memory" to retain the coiled shape. Electrical insulation materials such as urethane and nylon also provide superior "memory" characteristics compared to the PVC coating historically used for telephone cords.

Figure 14:
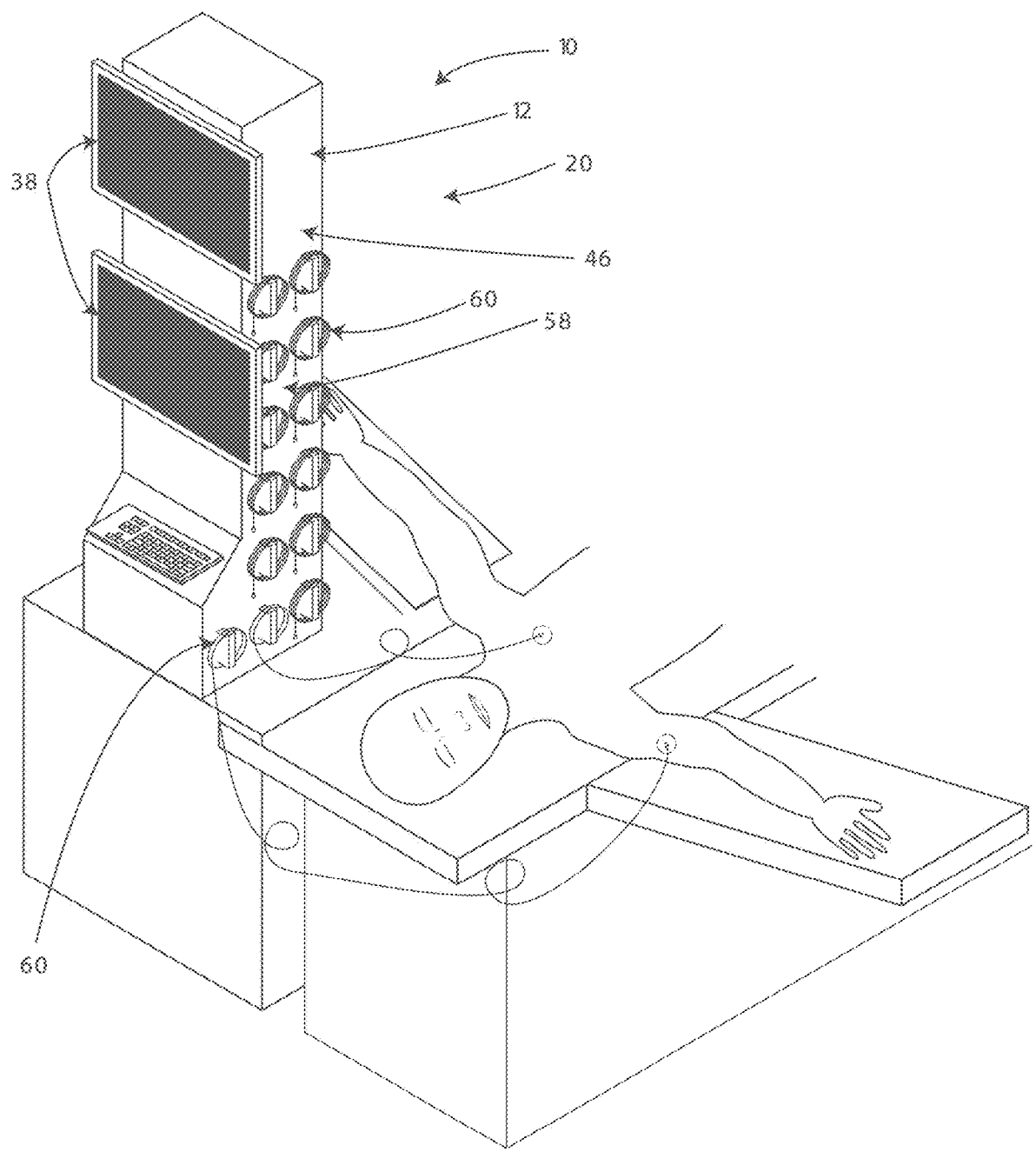
FIG. 14 shows a perspective view of the illustrative system of FIG. 10 with two of the cables unwound and attached to the patient, in accordance with at least one example.

As shown in FIG. 14, these larger coils 60 are easily stretched because the elongation is accomplished primarily by the lateral movement of adjacent coils, perpendicular to the plane of the individual coils, basically elongating the tubular shape, a movement that is minimally opposed by the "memory" of the molding process. This is in contrast to an attempt to unwind each of the individual coils 60, a movement that is maximally opposed by the "memory" of the molding process. The larger coils 60 easily stretch laterally between each adjacent coil 60 and stretch minimally in the plane of each coil 60. This is identical to the principals the make a "slinky" work, very easy to stretch in the direction of the coiled tube but nearly impossible to unwind and individual coil. The larger coils 60 easily stretch laterally between each adjacent coil 60 which makes them far less prone to twisting and tangling than if an individual coil 60 is "unwound."

In some embodiments the coils 60 of the cable management system 58 created by extrusion molding an electrically insulating plastic sheath over the wires of the cable. In some embodiments the coils 60 of the cable management system 58 are created by extrusion molding a coil of plastic tubing 80 and then inserting the wires of the cable 78 into the tubing 80 as a second operation. In some embodiments, when tubing 80 is used to create the coils 60, the tubing 80 may be 0.25-0.6 inches in outside diameter. Larger tubing 80 diameters may work better with larger coil 60 diameters. In some embodiments the preferred tubing material is urethane. Other tubing materials are anticipated, including but not limited to nylon and PVC.

There are several advantages to adding a cable 78 to a molded coil 60 of plastic tubing 80 as a second process rather than molding the insulation layer of the cable into a coiled shape. The extruded tubing 80 has a thicker outer layer of very uniform extrusion thickness, which results in a more durable outer layer with superior memory for the coiled shape 60.

In some embodiments, one construction is to add 0.5-4 feet of standard cable 78 to the distal end of the coiled tubing 80 and pull the individual wires through the coiled tubing 80 to the proximal end of the tubing 80. In this case, the distal 0.5-4 feet may be a much more flexible cable 78 than the coiled tubing 80 because the cable 78 is not intended to retain a memory for a coiled shape. The tubing 80 and the cable 78 may be made of different materials, or different durometers of the same material, or different stiffness's of the same material for their outer insulation layers, each of which optimize the intended function (coil memory vs. flexibility). The 0.5-4 feet of standard cable 78 attached to the distal end of the coiled tubing 80 also presents a lower profile as it encounters the patient. For example, if the cable 78 is an EKG lead laying on top of the patient's chest, a flexible non-coiled wire or cable 78 will be more comfortable than coiled tubing 80.

In some embodiments, this design optimizes the recoil function at the proximal coiled tubing 80 portion of the cable. This design also optimizes the patient interface for flexibility, low profile and comfort by transitioning from the coiled tubing 80 to a standard cable 78 for the distal 0.5-4 feet.

In some embodiments as shown in FIGS. 12 and 13, the proximal end 62 of the proximal coil 60 is firmly attached to the side 46 of the module 10 facing the patient, in order to prevent the tubing 80 from twisting when removed from the storage bracket 66. The firm non-twisting attachment may preferably orient the plane of the first coil 60 and thus the planes of all of the coils 60, essentially parallel to the plane of side 46. Orientation of the first coil 60 to be parallel to the plane of side 46 makes the entire stack of coils 60 naturally form into a tubular or stack shape for easy storage. In some embodiments, a storage bracket 66 protrudes from the side 46 to provide a storage location for the naturally coiled tubing 80 cables and hoses. The natural coiled shape makes loading the tubular stack of coils 60 onto the storage bracket 66 so easy that it almost occurs spontaneously.

Figure 15:
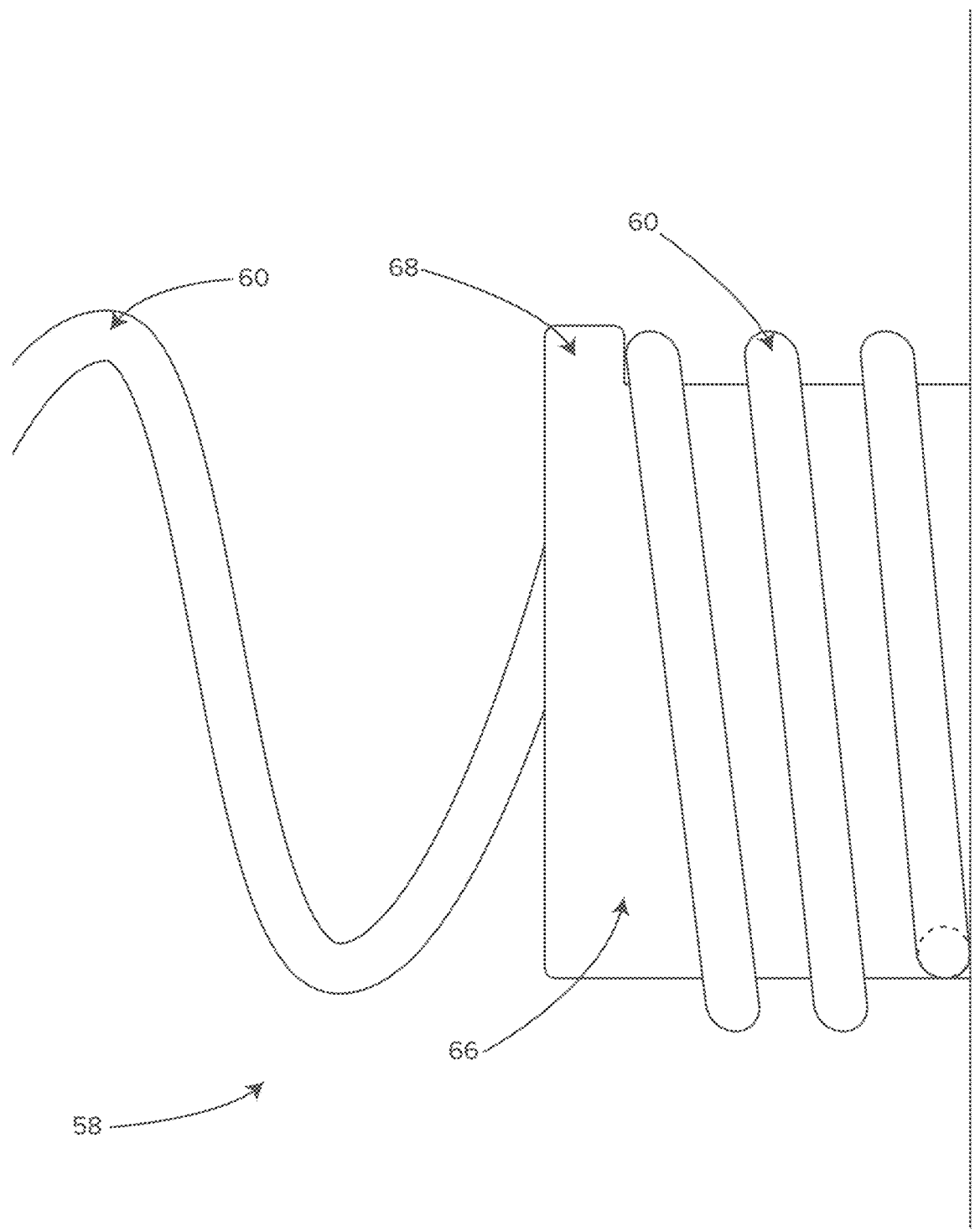
FIG. 15 shows a rear view of a storage bracket and cable of the illustrative system of FIG. 10, in accordance with at least on example.

In some embodiments as shown in FIGS. 12, 13 and 15, the storage bracket 66 may include a retaining lip 68 that helps to prevent the coils 60 from inadvertently slipping off of the storage bracket 66. In some embodiments as shown in FIG. 15, the retaining lip 68 may also advantageously allow one or more individual coils 60 to be removed from the storage bracket 66 while retaining the remaining coils 60. This conveniently allows variable lengths of tubing, cables and hoses to be extended from the cable and hose management system 58. Cables and hoses that need to reach further, for example to the foot of the surgical table or to the arm-board on the opposite side of the surgical table, may require all of the coils 60 to be removed from the storage bracket 66 and stretched to their limits. Alternately, if a given cable or hose is only traveling a short distance, for example to the patient's chest or the head end of the mattress, perhaps only one or two individual coils 60 may be removed from storage bracket 66 and the remaining coils 60 are retained on the bracket 66. This minimizes the excess cable and hose from cluttering and tangling.

In some embodiments, with minimal force six 3 inch diameter coils 60 of this invention can be stretched perpendicularly to the plane of the individual coils 60, a distance of more than 4 feet. In the stretched configuration, the coils 60 preferably still exhibit recoil forces but the recoil forces are not so great as to pull the plug or sensor 82 loose from the patient connection.

The recoil of the molded coils 60 naturally cause the adjacent individual coils 60 to form into an orderly stack or tubular shape which can easily be loaded onto the storage bracket 66. Storing the stack of individual coils 60 on a storage bracket 66 helps the individual coils 60 and the stack of coils 60 "rest" and thus may retain their molded "memory" for a coiled shape over years of use.

In some embodiments, the natural recoil of the coils 60 will advantageously prevent the electrical plug 82 or hose connector from touching the floor when not loaded on the storage bracket 66 and not in use. The natural recoil of the coils 60 may advantageously prevent the plug 82 or hose connector from touching the floor even if the coiled tubing 80, cable 78 or hose is not properly stored on the storage bracket 66. Keeping cables 78 and hoses off of the floor vastly reduces their contamination and need for cleaning. This is in contrast to the current cable and hose situation where they typically lay on the floor when not in use.

In some embodiments the cable and hose management system 58 using coiled tubing 80 may be adapted to a location that is remote to the module 10. In some embodiments the cable and hose management system 58 using coiled tubing 80 may be adapted to the outer shell or case of another piece of equipment such as a patient warming system or a patient monitor. In some embodiments the cable and hose management system 58 using coiled tubing 80 may be adapted to a free-standing pod that is attached to the side of the surgical table 22 and is used to distribute and connect the distal end of the wires contained in a trunk cable, to the patient 24 and surgical table 22. In each of these instances, the coiled tubing 80, cable 78, mounting and storage bracket 66 previously described may be advantageously used to store the cables and hoses for various surgical and anesthetic equipment and monitors.

In some embodiments, power cords, communication cables, air, oxygen and vacuum hoses from the ceiling can be more safely and unobtrusively connected to the top of a taller tower-like upper section 20.

Traditionally, electric power cords, air hoses, oxygen hoses, vacuum hoses and communications wires hanging from the ceiling of the OR, disrupt workflow and create hazards to personnel movement when not hooked to their intended equipment. Traditionally, electric power cords, air hoses, oxygen hoses, vacuum hoses and communications wires hanging from the ceiling of the OR are limited in length so as to not touch the floor when hanging free. This limited length severely limits the movement and flexibility of location for the anesthesia gas machine or any other any other equipment to which they may be hooked. The gas machine must be located directly below the ceiling outlets.

In some embodiments, power cords, air hoses, oxygen hoses, vacuum hoses and communications wires are coiled similarly to coils of the cable management system, disclosed herein. In some embodiments, the coils are created by extrusion molding a coil of plastic tubing and then inserting the wires of the cable or cord into the tubing as a second operation. In some embodiments, the coils are created by extrusion molding a coil of plastic tubing for air hoses, oxygen hoses and vacuum hoses. In some embodiments, the coiled plastic tubing portion comprises the proximal end of the cable or hose, the end attached to the ceiling. The coiled tubing may be any length but may preferably be 6-16 feet when stretched.

In some embodiments, nylon may be the preferred material for the coiled tubing because of its superior springiness and memory. Other materials are anticipated. The coiled portion allows the cables and hoses to be stretched and elongated, which greatly increases the floor area where the given OR equipment may be located, increasing the flexibility of the OR layout. The stretchable tubing also decreases the number of ceiling connection locations that are necessary to provide connection options for the whole OR.

In some embodiments, a "tail" portion of relatively straight, relatively flexible cord, cable, tubing or hose is attached to the distal end of the coiled tubing hanging near the ceiling. In some embodiments, the transition between the coiled portion and the tail portion does not require the connection of two dissimilar materials. In some embodiments, the coiled tubing may be simply be straightened in a heating process that relaxes the memory of the coil. In this case the coiled portion and the tail portion are the proximal and distal ends of the same piece of tubing. In some embodiments, the tail portion hangs down to a level that can be reasonably reached by a person standing on the floor, and yet not hang down far enough to hit OR personnel in the head when not attached to equipment. In some embodiments, the distal end of the tail portion terminates approximately 7 feet above the floor. The coiled portion allows the stretched cables and hoses to recoil when not hooked to equipment, thus naturally lifting the distal connectors up to a level that will protect OR personnel from being hit in the head. The relatively straight tail portion reduces visual clutter hanging from the ceiling and reduces the chances of adjacent cables and hoses tangling when connected to a given piece of equipment.

Waste air is currently discharged from every piece of electrical and electromechanical surgical and anesthesia equipment in the operating room. The discharged air is simply blown into the operating room, usually near the floor where the given piece of equipment is located. Waste heat and air discharged near the floor has been shown to form into rising convection currents of heated air that can carry infectious contaminates from the floor up and into the sterile surgical field. Waste heat vented near the floor is a dangerous surgical infection risk. Contaminated waste air blowing from heater-cooler units has been genetically linked to heart valve infections.

The problem is that all electronic and electromechanical equipment produce waste heat that must be dissipated or the equipment will be damaged. Typically, this is accomplished with a cooling fan that simply discharges the waste heat and waste air into the operating room. Additionally, some pieces of surgical and anesthesia equipment such as forced-air warming, produce heated waste air on purpose. The waste air and heat from forced-air warming can cause contamination of the sterile surgical field and cause implant infections. Discharging waste heated air into the operating room, especially close to the surgical table and sterile field, is dangerous because it causes contamination of the sterile filed. Therefore, this waste air and heat must be vacuumed, processed and safely discharged in order to prevent sterile surgical field contamination and catastrophic infections.

In other examples, the vacuumed air from the surgical field such as surgical smoke evacuation or ventilation deadzone evacuation or waste oxygen and alcohol evacuation, must also be processed and safely discharged.

Figure 16:
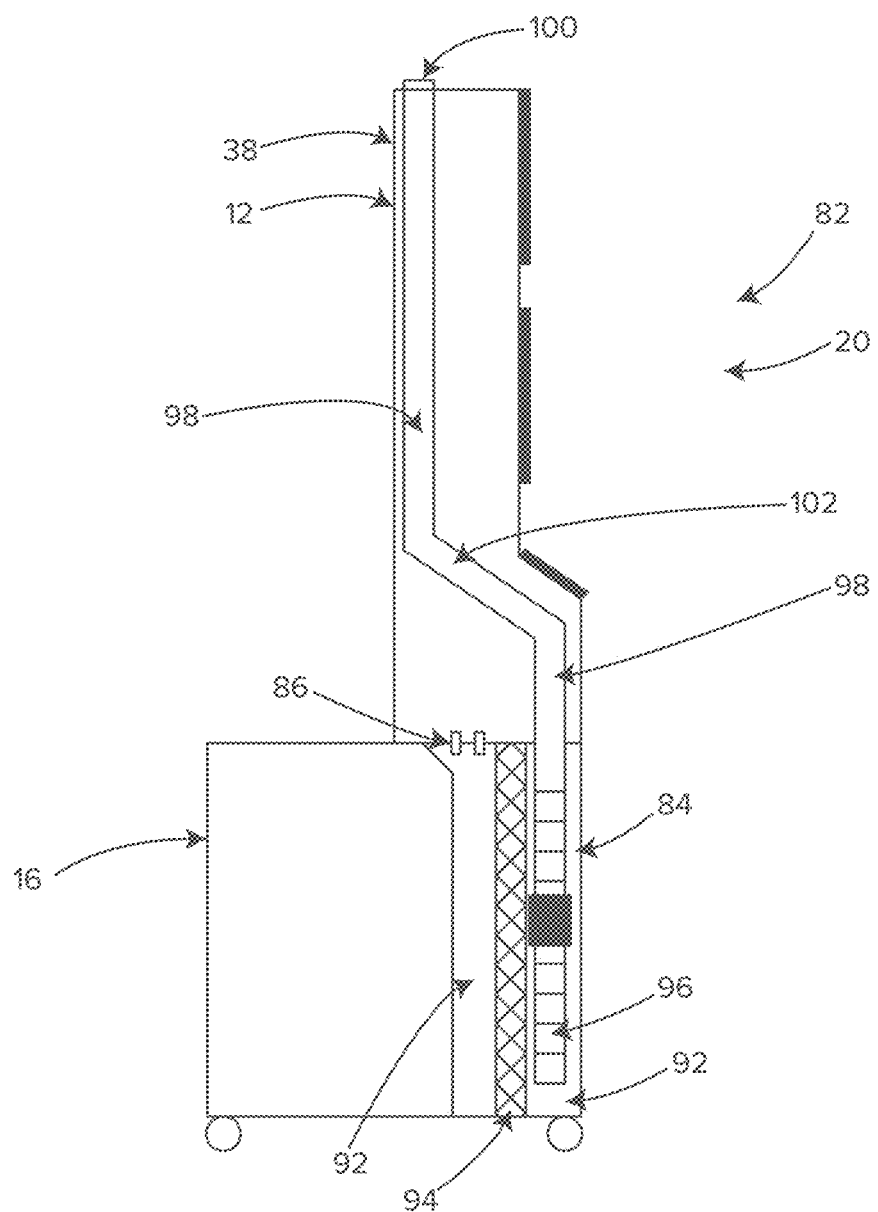
FIG. 16 shows a side view depicting internal components of an illustrative waste air system that can be used with the system of FIG. 10, in accordance with at least one example.
Figure 17:
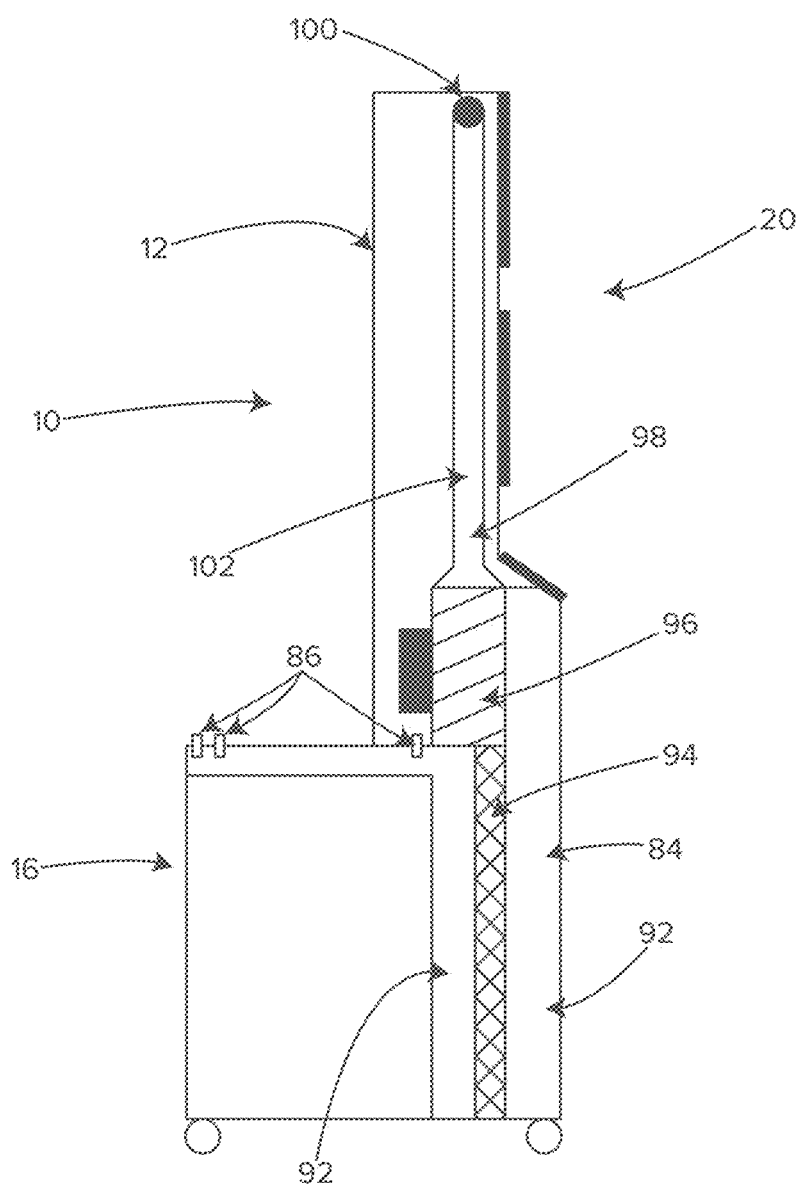
FIG. 17 shows a side view depicting internal components of another illustrative waste air system that can be used with the system of FIG. 10, in accordance with at least one example

In some embodiments as shown in FIGS. 16 and 17, the module 10 includes a waste air management system 84. The waste air management system 84 may include an inlet vent 86 with a connector 88 that can connect to a hose 90 designed to vacuum waste air from a specific location. In some embodiments, it may be advantageous to have the various air and vacuum hoses 90 connected to the waste air management system 84 by way of "keyed" connections 88 so that they are not mistakenly attached to the wrong inlet 86 or outlet 118 port. For example, the hose connection 88 may be any other shape than the traditional round shape; triangular, square, five or six sided, oval, diamond shaped or any other shape. In some embodiments, the inlet vent 86 on the waste air management system 84 and the connectors 88 on the specific hose 90 may be color coded for easy identification.

In some embodiments, the waste air management system 84 includes an air plenum 92 containing an air filter 94. The filter 94 may advantageously be a HEPA (99.97% efficient) or near HEPA filter. One or more air inlet vents 86 can allow waste air to enter the plenum 92 from either the equipment housed in the module 10 or from external equipment sources. In some embodiments, a low filtration efficiency pre-filter may be placed near the inlet vents in order to prevent organic contaminates such as airborne body fluids, bone or tissue fragments, from entering and contaminating the interior of the waste air management system 84.

A fan 96 propels the waste air through the filter 94 and exhausts the air from the plenum 92 into a substantially vertical vent tube 98. In some embodiments, the substantially vertical vent tube 98 extends upward to a height of more than 5 feet above the floor, before discharging the processed waste air from outlet vents 100 near the top of the substantially vertical vent tube 98. In some embodiments, a sock-like filter may be added to the outlet vent in order to diffuse the outlet air and muffle any fan noise.

In some embodiments, the inlet vent 86 is attached to an air plenum 92 located in the module 10. Preferably, the air plenum 92 is designed to direct inlet air through a filter 94 and fan 96 before safely discharging it into the operating room. In some embodiments, the filter 94 is located in the airflow path before the fan 96 so that the air contacting the fan 96 has been cleaned by the filter 94. Contaminated air has been shown to contaminate fans, which are very difficult to clean and may aerosolized contaminates into the discharged air. In some embodiments, the fan 96 may be located between the air inlet vent 86 and the filter 94. In some embodiments, all of the ducting and plenums of the waste air management system 84, are accessible on their internal surfaces for cleaning and decontamination.

In some embodiments, the filtered waste air is then directed through ducting 102 which functions as a substantially vertical vent tube 98, up the tower-like upper section 20, to be vented 100 out near the top of the tower-like upper section 20. In some embodiments, the filtered waste air is then directed through the cowling 12 of the tower-like upper section 20 which functions as a substantially vertical vent tube 98, to be vented out 100 near the top of the tower-like upper section 20. In some embodiments, a sock-like filter may be added to the outlet vent in order to diffuse the outlet air and muffle any fan noise.

Figure 18:
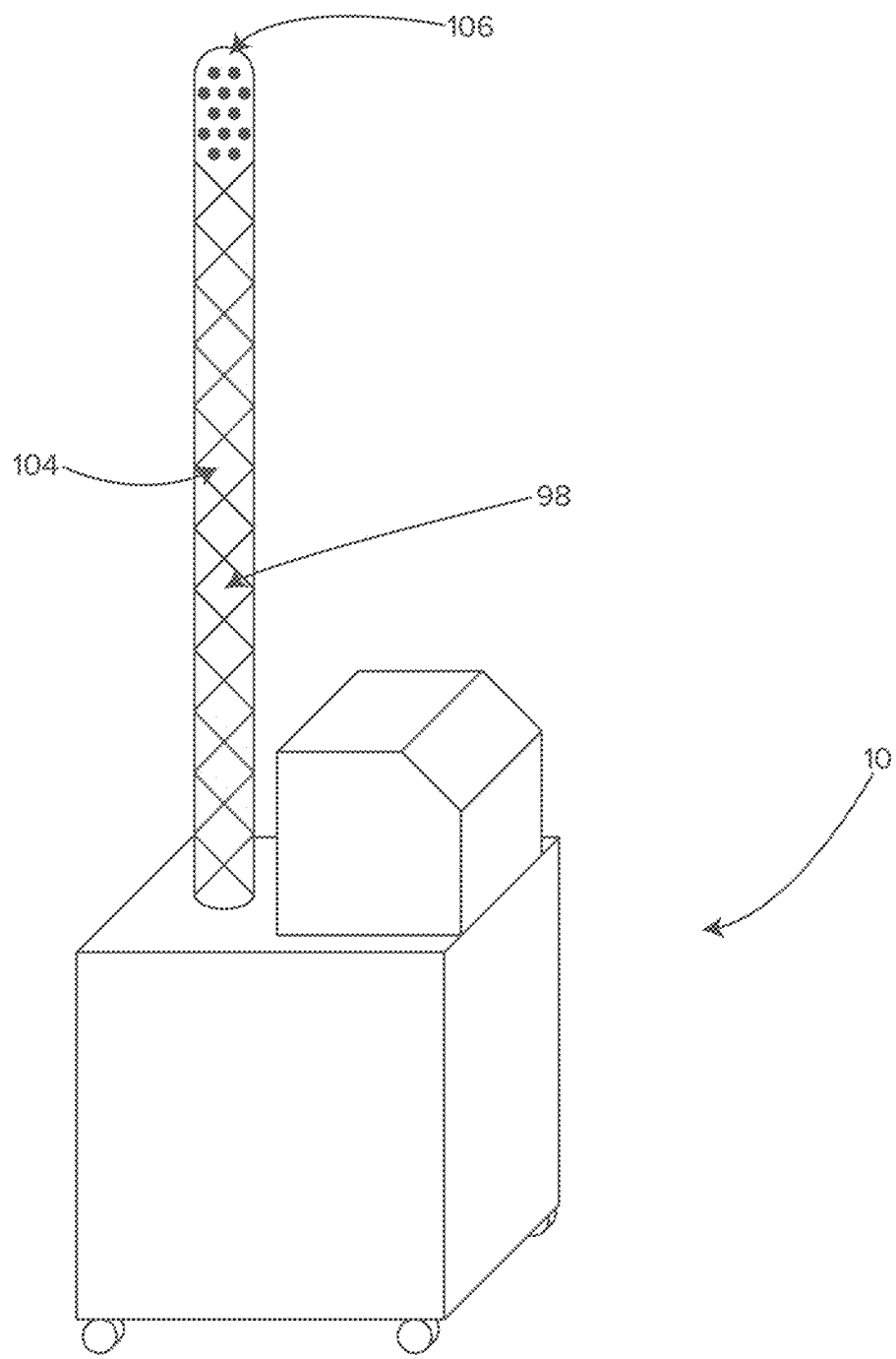
FIG. 18 shows a side perspective view of an illustrative storage, airflow and cable and cord management system including an example vent tube.
Figure 19:
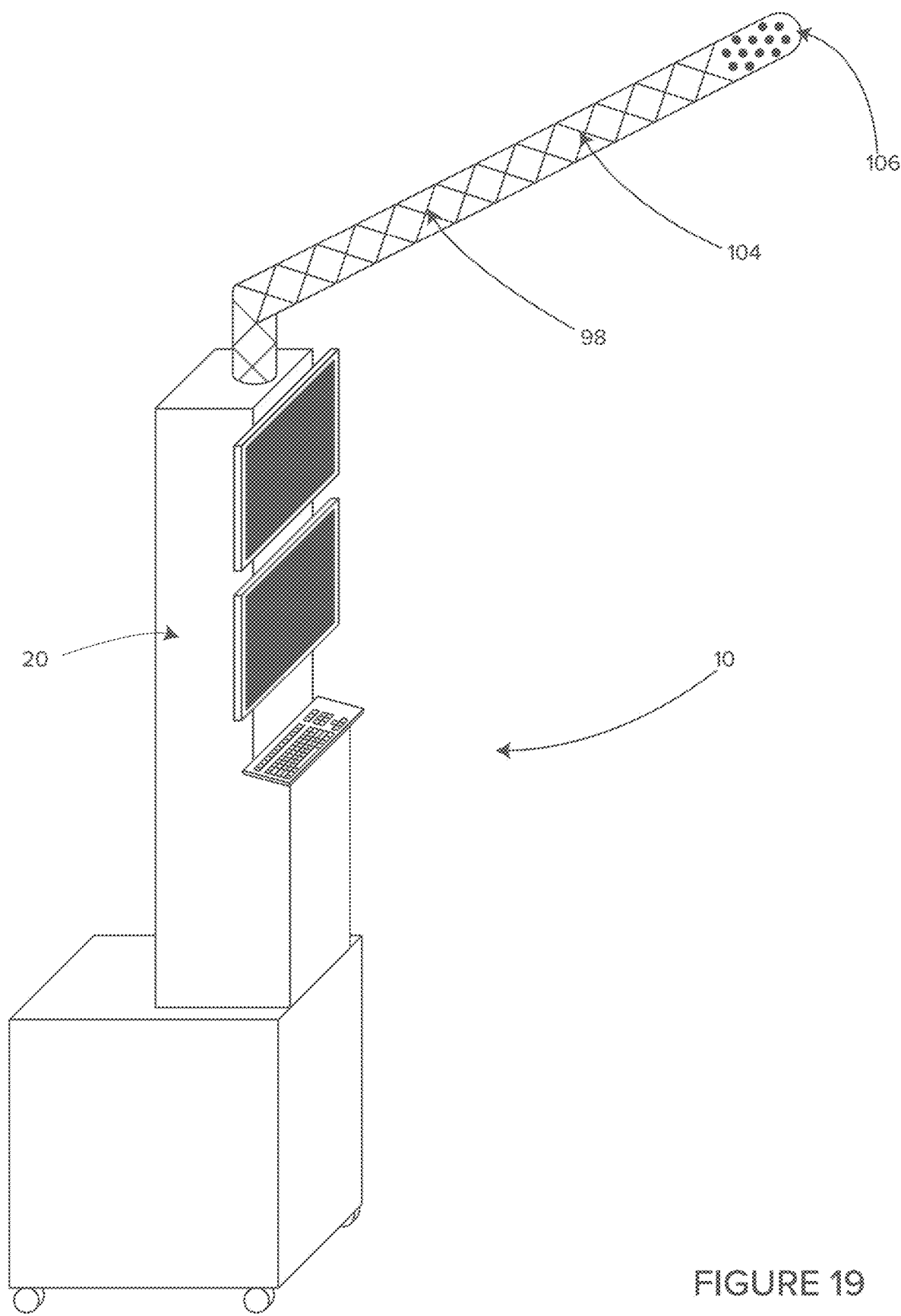
FIG. 19 shows a side perspective view of another example storage, airflow and cable and cord management system including another example of a vent tube.

In some embodiments, the substantially vertical vent tube 98 may be a rigid tube. In some embodiments, the substantially vertical vent tube 98 may be the tower-like upper section 20 of the module 10. In some embodiments as shown in FIGS. 18 and 19, the substantially vertical vent tube 98 is an inflatable, collapsible tube 104 made of fabric, plastic film or fabric laminated to or coated with a plastic film. In some embodiments, the inflatable, collapsible tube 104 may be disposable. In some embodiments, the distal end 106 of the inflatable, collapsible tube 104 is made of woven or non-woven fabric that serves both as a flow obstruction to increase the pressure in the tube and also as a final filter before the waste air is discharged.

In some embodiments, the inflatable, collapsible tube 104 includes a substantially sealed distal end 106 with one or more holes in the walls of the tube to allow the air to escape but create a flow obstruction causing the pressure within the inflatable, collapsible tube 104 to increase. The increased pressure in the inflatable tube 104 causes the inflatable tube 104 to assume an erect shape. In some embodiments as shown in FIG. 18, the erect inflatable, collapsible tube 104 extends substantially vertically in order to terminate at a height of more than 5 feet above the floor. In some embodiments as shown in FIG. 19, the erect inflatable tube 104 extends diagonally at an upward angle. Depending on the direction of the angled portion, the distal top end 106 of the inflatable tube 104 may be positioned outside of the operating room ventilation flow field for added safety.

In some embodiments, the waste air management system 84 produces a relatively high-volume airflow (10-100 CFM)

at relatively low positive and negative (vacuum) pressures (less than 2 inches of water). This allows the fan 96 in the lower section 14 to operate at relatively slow speeds under normal conditions in order to minimize the fan noise. The large volume of the bulbous lower section 16 of the module 10 advantageously allows the fan 96 of the waste air management system 84 to be relatively large in diameter. Large diameter fans may produce high volume airflows with relatively slow fans speeds.

In some embodiments, the waste air management system 84 may safely process the waste air that is the by-product of equipment contained within the module 10. In some embodiments, inlet vents 86 into the plenum 92 are in fluid connection with the interior space of module 10. Waste heated air that has cooled the equipment in the module 10, may be vacuumed from the equipment space into the plenum 92 for safe processing and discharge.

In some embodiments, the waste air management system 84 may safely process the waste air that is the by-product of other surgical and anesthesia equipment. Waste air producing surgical equipment includes Heater-cooler units (HCU) that produce contaminated waste heated air that needs to be processed and safely discharged. In this case, the waste heated air is a by-product of cooling the refrigeration compressor of the HCU that has been contaminated by water leaking from the water chiller. Forced-air warming units (FAW) also produce contaminated waste heated air that needs to be processed and safely discharged. The FAW systems exhaust waste air from under the surgical drape where it may escape from under the surgical table near the floor. In some embodiments, this waste heated air from FAW can be contained and vacuumed up for safe disposal. Electrosurgical units and other surgical equipment also produce waste heated air that needs to be processed and safely discharged. Conventionally, these various pieces of equipment in the operating room are not stored proximate one another in a module 10 (e.g., module including a cowl or seal) with a common waste air management system 84. Anesthesia monitoring is generally located in the non-sterile anesthesia field, while the surgical focused equipment is located distal from the anesthesia monitors.

Figure 20:
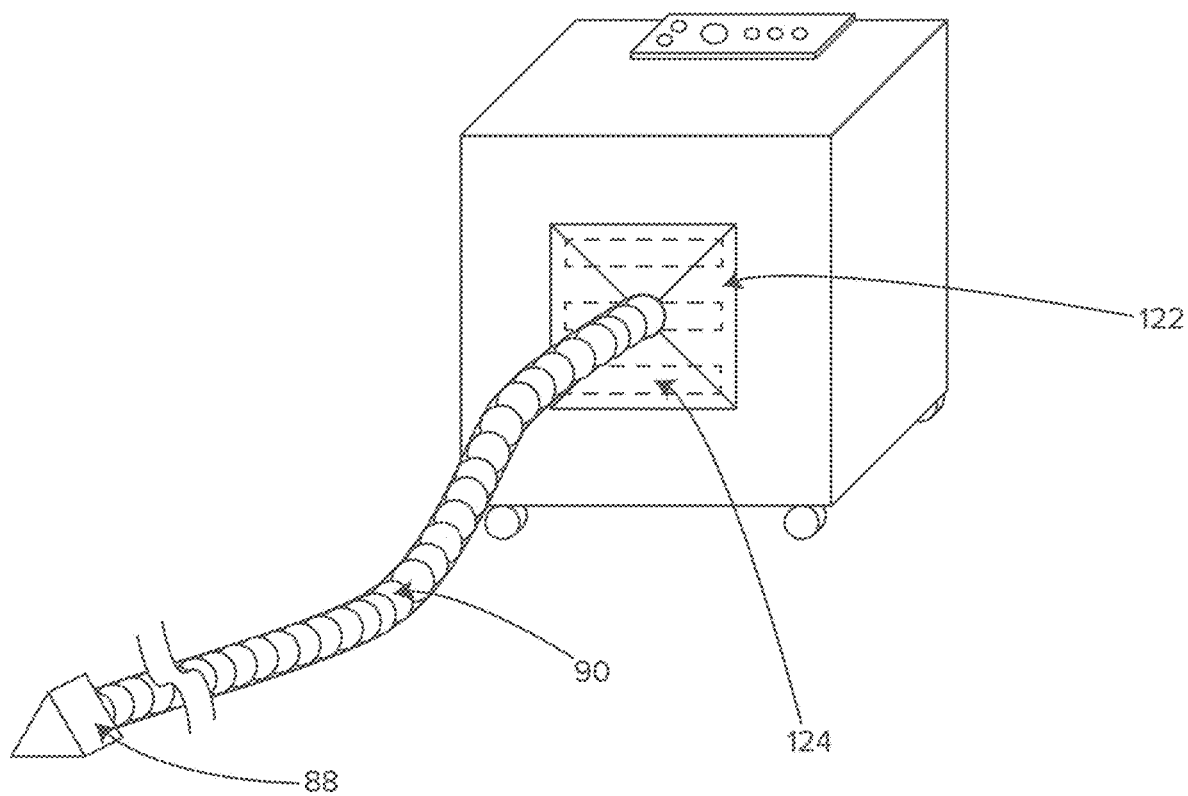
FIG. 20 shows an example waste air management system including an example vacuum tube.

In all of these examples, a vacuum hose 90 may terminate near or in the waste heat and waste air producing equipment. In some embodiments, it may be advantageous to attach a collection "funnel" to the end of the vacuum hose in order to direct the waste air into the hose end. In some embodiments as shown in FIG. 20, the funnel 122 may be a rigid construction if it is gathering air from the outlet vent of a specific piece of equipment such as a heater-cooler unit. In some embodiments, the funnel 122 may be a flexible construction, for example a sheet of plastic film, if it is gathering air from the discharge area of a forced-air warming blanket. In some embodiments, the perimeter of the sheet of plastic film may be adhesively bonded to the open end of the underside of a FAW blanket.

In some embodiments, the hose 90 for the evacuation of waste air from surgical and anesthesia equipment may be lightweight, thin walled, inexpensive hose, ½-2 inches in diameter. The hose 90 may advantageously be made of polyethylene, polypropylene, PVC or other plastic materials. The hose 90 may advantageously be corrugated. In some embodiments, the proximal end of the hose 90 for the evacuation of waste air from surgical and anesthesia equipment is a uniquely shaped connector 88 such as square or triangular for example.

In some embodiments, the waste air management system 84 may safely process the waste air and smoke that is the by-product of the electro-cautery used for tissue cutting and coagulation. This smoke has been shown to be a hazard to the surgical staff because it may contain carcinogens and may contain viruses.

In some embodiments, the smoke evacuation suction used for evacuating electrosurgical smoke may include a hose 90 hooked to a vacuum source. The distal end of the hose 90 may be located near the surgical wound that is being cauterized or tissue being cut with electro-cautery. The distal end of the hose 90 may be attached to the active electrode of the electro-cautery or it may be located near the surgical wound. If it is located near the surgical wound, the distal end of the hose 90 may be secured to the sterile surgical drape with an adhesive.

In some embodiments, the proximal end connector 88 of the smoke evacuation hose 90 for smoke evacuation from the surgical field, may be attached to the inlet vent 86 of the waste air management system 84. The smoke from the electro-cautery may be safely vacuumed from the surgical field and then filtered in the waste air management system 84. In some embodiments, the hose 90 for smoke evacuation may be lightweight, thin walled, inexpensive hose, ⅜-¾ inches in diameter. The tubing may advantageously be made of polyethylene, polypropylene, PVC or other plastic materials. The hose 90 may advantageously be corrugated. In some embodiments, the proximal end connector 88 of the smoke evacuation hose 90 is a uniquely shaped connector 88 such as square or triangular for example.

Figure 21:
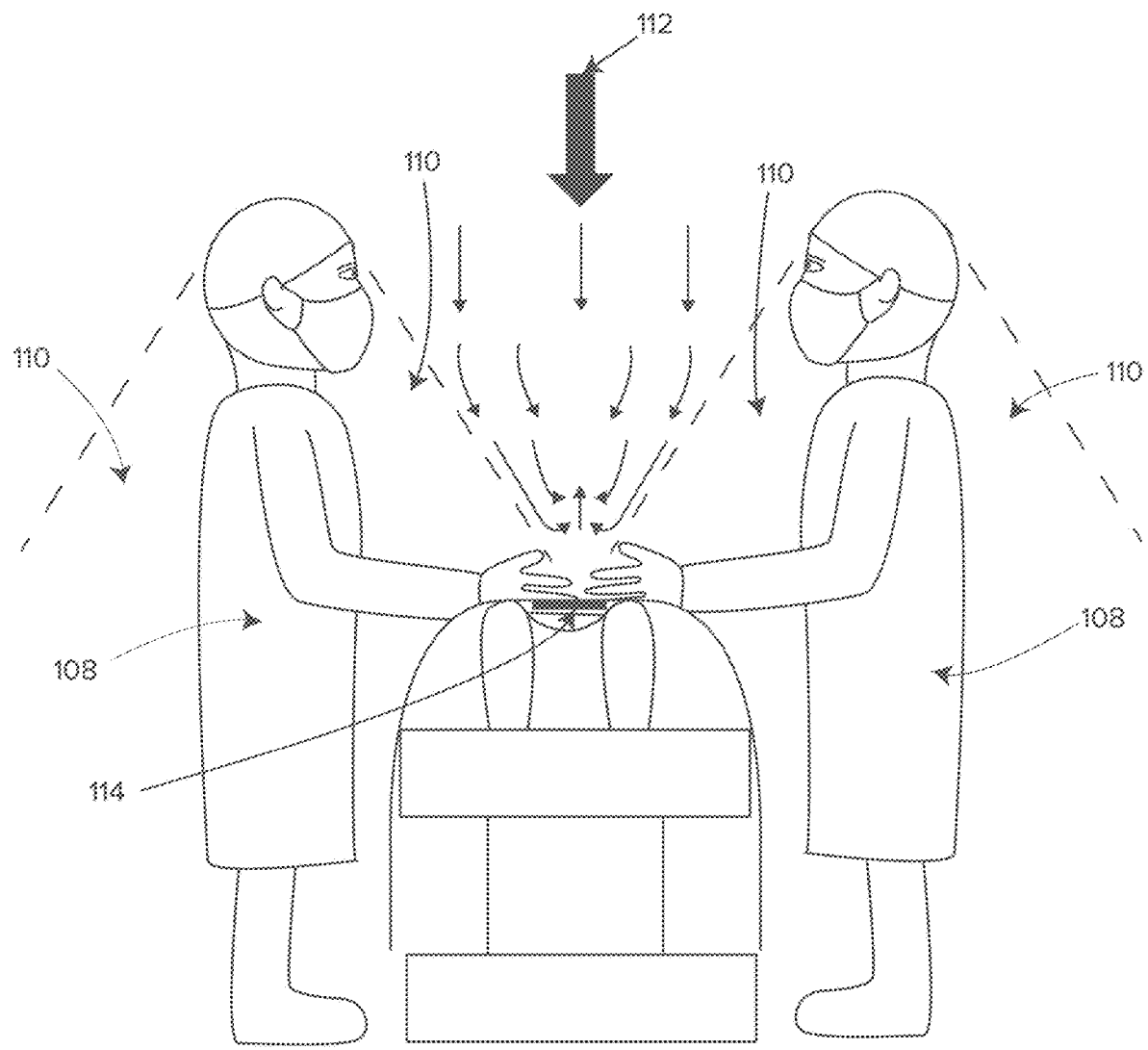
FIG. 21 shows an example surgical field depicting flow-boundary dead zones.

In some embodiments, the waste air management system 84 may safely process the waste air that is the by-product of operating room ventilation optimization system. It has been shown that flow-boundary dead zones naturally form around the surgeons and in front of anesthesia screen. This is a natural phenomenon that occurs anytime a fluid (or gas) flows next to a non-moving object—a boundary layer of non-moving fluid (or gas) is formed as shown in FIG. 21. These flow-boundary "dead zones" 110 that form around the surgeons 108 and staff, effectively prevent the downward ventilation airflow 112 from the ceiling of the operating room from reaching the open surgical wound 114. When the ventilation airflow 112 stops, contaminating particles and bacteria that had been kept airborne by the moving air, are allowed to settle into the wound 114. When the ventilation airflow 112 slows or even stops due to dead zone 110 interference, gravity takes over and the airborne contaminates settle into the wound 114 where they may cause infections. We have shown that the negative effects of these dead zones 110 can be minimized by vacuuming out the dead zone air, which allows the ventilation air 112 to flow past the wound 114, keeping airborne contaminating particles and bacteria, airborne in the moving air where they do no harm.

In some embodiments, the ventilation optimization system includes ventilation dead zone 110 evacuation; by vacuuming the air from the flow-boundary dead zones 110 that naturally form in front of the surgeons 108 and anesthesia screen 30, the interference of the flow-boundary layers with the operating room ventilation 112 is in reduced. This allows the ventilation airflow 112 from the ceiling to reach the wound 114 unimpeded by a flow-boundary dead zone 110. These interfering dead zones 110 of non-moving air can be evacuated by placing the distal end of vacuum hoses 90 into the dead zone 110. The evacuated air should then be processed in order to safely discharge the air, back into the operating room. In some embodiments, the distal end of the dead zone evacuation hose 90 may be secured to the sterile surgical drape with an adhesive.

In some embodiments, the proximal end of the dead zone evacuation hose 90 exiting from the surgical field may be attached to the inlet vent 86 of the waste air management system 84. The waste air from the dead zone evacuation may be safely filtered in the waste air management system 84. In some embodiments, the hose 90 for dead zone evacuation may be lightweight, thin walled, inexpensive hose, ½-2 inches in diameter. The hose 90 may advantageously be made of polyethylene, polypropylene, PVC or other plastic materials. The hose 90 may advantageously be corrugated. In some embodiments, the proximal end of the dead zone evacuation hose 90 is a uniquely shaped connector 88 such as square or triangular for example.

In some embodiments, the waste air management system 84 may be used to evacuate the air under the surgical drape (e.g., 30 in FIG. 4), especially near the patient's head, neck and chest (e.g., near 24 in FIG. 4). Alcohol from the surgical prep solution may pool under the drapes and then evaporate. Waste oxygen from an unrestricted oxygen supplementation system such as nasal prongs or facemask may allow waste oxygen to pool under the surgical drape, especially near the patient's head, neck and chest. Then, add a spark from either the electro-cautery or a laser and highly dangerous operating room fires occur far too frequently. Even the surgical drape can burn in the presence of an oxygen-enriched environment. It may be advantageous to remove the air and oxygen and alcohol vapors trapped under the surgical drape.

Figure 22:
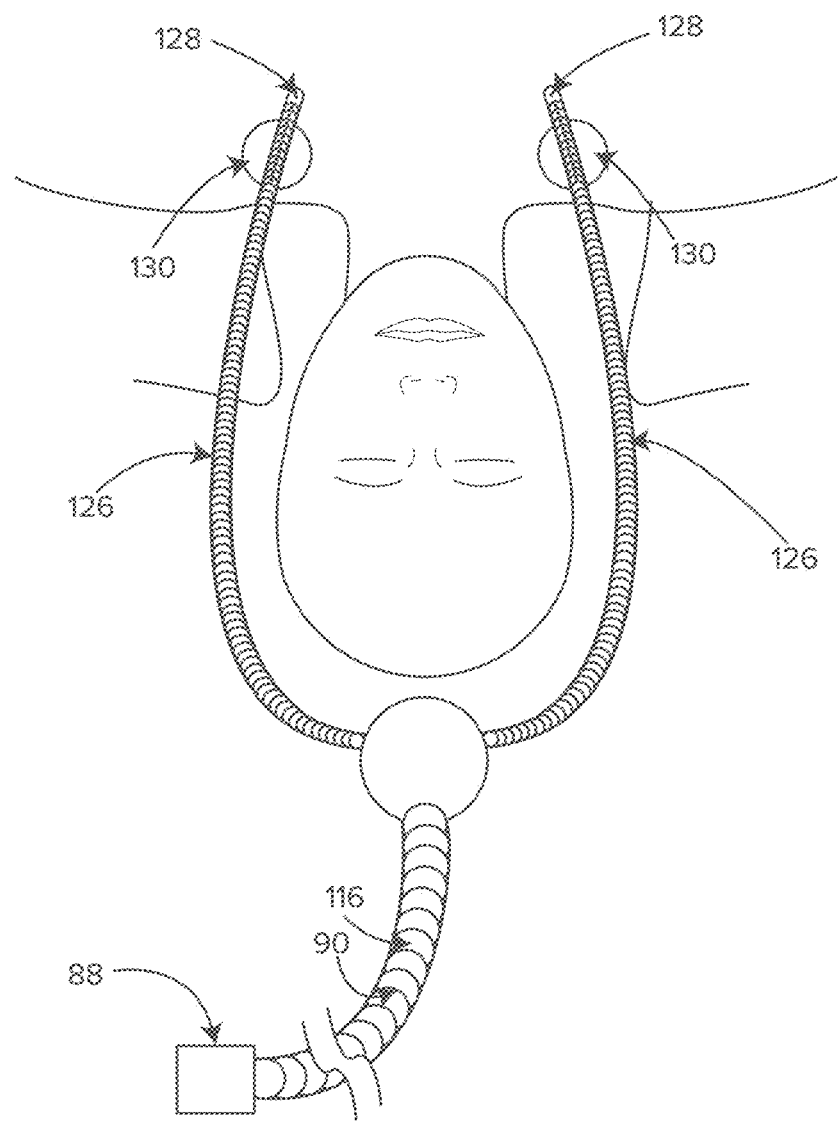
FIG. 22 shows an example of an air dilution system that can be used with the systems described herein.

In some embodiments as shown in FIG. 22, a vacuum hose 90 may be placed near the shoulders, chest and neck of the patient. The distal end of the oxygen/alcohol vacuum hose 90 may terminate in a single hole, multiple holes or even multiple smaller hose "tentacles" 126, each with one or more holes 128 and each located near the patient. In some embodiments, longer "tentacle" oxygen/alcohol vacuum hoses 126 may extend over the patient's chest or along their sides to terminate with the holes 128 near the abdomen. In some embodiments, the distal end of the "tentacle" hoses 126 may be secured to the patient with an adhesive patch 130.

In some embodiments, the proximal end of the oxygen/alcohol evacuation hose 90 exiting from the surgical field may be attached to the inlet vent 86 of the waste air management system 84. The waste air from the oxygen/alcohol evacuation may be safely filtered in the waste air management system 84. In some embodiments, the hose 90 for oxygen/alcohol evacuation may be lightweight, thin walled, inexpensive hose, ⅜-1 inch in diameter. The hose 90 may advantageously be made of polyethylene, polypropylene, PVC or other plastic materials. The hose 90 may advantageously be corrugated. In some embodiments, the proximal end of the oxygen/alcohol evacuation hose 90 is a uniquely shaped connector 88 such as square or triangular for example.

In some embodiments, the waste heated air can be vacuumed by the waste air management system 84, filtered and discharged at a height that does not allow any waste heat to mobilize contaminates normally resident near the floor, up and into the sterile field. In other words, the air discharged from the waste air management system 84 may advantageously be at a height that is greater than 4 feet off of the floor. In some embodiments, the air discharged from the waste air management system 84 may be diverted and used as a source of positive pressure air.

In some embodiments, the waste air management system 84 may be used to dilute the air under the surgical drape (e.g., 30, FIG. 4), especially near the patient's head, neck and chest. Alcohol from the surgical prep solution may pool under the drapes and then evaporate. Waste oxygen from an unrestricted oxygen supplementation system such as nasal prongs or facemask may allow waste oxygen to pool under the surgical drape, especially near the patient's head, neck and chest. Then, add a spark from either the electro-cautery or a laser and highly dangerous operating room fires occur far too frequently. It may be advantageous to dilute the air and oxygen and alcohol vapors trapped under the surgical drape by blowing fresh air into the space under the drapes.

In some embodiments as shown in FIG. 22, an air hose 116 may be configured to be placed near the shoulders, chest and neck of the patient. The distal end of the oxygen/alcohol dilution air hose 116 may terminate in a single hole, multiple holes or even multiple smaller hose "tentacles" 126, each with one or more holes 128 and each located near the patient. In some embodiments, longer "tentacle" oxygen/alcohol dilution air hoses 126 may extend over the patient's chest or along their sides to terminate with the holes near the abdomen. In some embodiments, the distal end of the "tentacle" air hoses 126 may be secured to the patient with an adhesive patch 130.

In some embodiments, the proximal end of the oxygen/alcohol dilution air hose exiting from the surgical table may be attached to the outlet connector 118 of the waste air management system 84. The outlet connector 118 may attach to the discharge side of the waste air management system 84 in order to utilize the positive pressure air being discharged from the system 84. In some embodiments, the air hose 116 for oxygen/alcohol dilution air may be lightweight, thin walled, inexpensive hose, ⅜-¾ inch in diameter. The air hose 116 may advantageously be made of polyethylene, polypropylene, PVC or other plastic materials. The air hose 116 may advantageously be corrugated. In some embodiments, the proximal end of the oxygen/alcohol dilution air hose 116 is a uniquely shaped connector 88 such as square or triangular for example.

In some embodiments, the output of the waste air management system 84 may be diverted into an air hose 116 that may be hooked to an inflatable "hover" mattress for moving the patient off of the surgical table at the end of surgery. The fan in the waste air management system conveniently provides the pressurized air for a "hover" mattress. Air may be diverted from the outlet side of the waste air management system 84, into an air hose 116 that is attached to a "hover" mattress. Since the "hover" mattress requires higher air pressure and higher airflow than the low velocity low pressure airflow normally produced by the waste air management system, the fan 96 of the waste air management system 84 may advantageously have two or more speeds. When the "hover" mattress is in use, the fan 96 of the waste air management system 84 may be speeded up to a higher RPM, thus delivering higher air pressures and air volumes, accepting a brief period of more fan noise. In contrast, under normal conditions when the "hover" mattress is not inflated, the fan 96 may be operated at a slower speed to reduce the annoying fan noise.

In some embodiments, when the output of the waste air management system 84 is diverted into an air hose 116 that is hooked to an inflatable "hover" mattress, the diversion valve may automatically close the normal exhaust ducting 102. Therefore, the air pressure in the diversion air hose 116 may be substantially increased, as required to inflate the inflatable "hover" mattress.

In some embodiments, one or more vacuum collection canisters for waste fluid and blood may be conveniently mounted on the module. A vacuum hose from the OR ceiling to the top of the tower of the module eliminates the need for that hose to traverse the floor from a wall outlet. Mounting the canisters on the module also allows the vacuum tubing from the surgical field to reach the canister without touching the floor.

In some embodiments, the one or more vacuum collection canisters may be accommodated in bucket-like recesses in the module, on the side facing away from the patient or the rear side of the module. In the case of multiple canisters, the hose from the surgical field may be split into two or more "tail" hoses that can each be hooked to the top of a collection canister. In some embodiments, two or more vacuum hoses may emerge from the module housing to be attached to the top of the collection canisters. In some embodiments, the two or more vacuum hoses each have a flow valve in the module, to control which canister is receiving the vacuum at any given time.

In some embodiments, optical or infrared fluid level sensors may be conveniently mounted in the wall of the bucket-like recesses in the module, adjacent the canister(s). Optical and infrared sensors rely on the relative increases absorption of blood and fluid compared to air in order to determine a fluid level. In some embodiments, the fluid level monitors may automatically activate or deactivate the vacuum valves to a given canister, thereby automatically shifting the blood and fluid flow to a new canister as the previous one is filled. In some embodiments, the surgical nurse can be wirelessly notified on their portable monitor, that one or more canisters are full of blood and fluid and may need to be replaced before the surgical procedure is finished.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

NOTES AND VARIOUS EXAMPLES

In an example 1, a module for housing electronic and electromechanical equipment for use during surgery, the module comprising:

a bulbous lower section;

a tower-like upper section; and the tower-like upper section being located on top of the front portion of the bulbous lower section;

wherein the rear portion of the bulbous lower section is configured to fit under an over-hanging obstruction such as the arm board of the surgical table.

1a.) The module of example 1, configured so that the rear of the tower-like upper section can be positioned adjacent the anesthesia side of one of the arm boards of the surgical table with the bulbous lower section fitting into the unused space under the arm board.

1b.) The module of examples 1 or 1a, wherein when the tower-like upper section is positioned adjacent the anesthesia side of one of the arm boards of the surgical table with the bulbous lower section fitting into the unused space under the arm board, the module can be accessed by staff simultaneously from both the anesthesia and surgical sides of the anesthesia screen.

1c.) The module of any preceding example, configured so that the rear of the bulbous lower section can be accessed from the surgical side of the arm board for hose and electrical connections from the surgical field to the equipment contained in the rack.

1d.) The module of any preceding example, wherein some or all of the module and the equipment housed in the module is enclosed in a water-resistant cowling.

1e.) The module of any preceding example, wherein water-resistant cowling is made of fiberglass, molded plastic, 3-D printed plastic, aluminum, stainless steel or other suitable water-resistant materials.

1f) The module of any preceding example, wherein the heavy electronic and electromechanical equipment is preferentially housed in the bulbous lower section, keeping the center of gravity close to the floor for added stability and tip resistance.

1g.) The module of any preceding example, wherein the tower-like upper section can accommodate the mounting of lightweight equipment controls, display screens and monitor screens at a convenient height for viewing and operating by a standing or sitting anesthesia provider.

1h.) The module of any preceding example, wherein the top of the tower-like upper section is more than 4 feet above the floor.

1i.) The module of any preceding example, configured so that power cables, communications cables, air hoses or vacuum hoses from the ceiling of the operating room can access the module near the top of the tower-like upper section.

1j.) The module of any preceding example, configured so that the module is supported by four or more caster wheels.

1k.) The module of any preceding example, configured so that the module is supported by a boom hanging from the ceiling of the operating room.

In an example 2, a module for housing and protecting electronic and electromechanical equipment for use in a hazardous location such as adjacent the surgical table where water, saline (salt water) and blood can be spilled during surgery, the module comprising:
a bulbous lower section;
a tower-like upper section; and
the rear portion of the bulbous lower section is configured to fit under an over-hanging obstruction such as the arm-board of the surgical table;
wherein at least some of the module and the equipment housed in the module is enclosed in a water-resistant cowling.

2a.) The module of any preceding example, wherein water-resistant cowling is made of fiberglass, molded plastic, 3-D printed plastic, aluminum, stainless steel or other suitable water-resistant materials.

2b.) The module of any preceding example, configured so that the rear of the tower-like upper section can be positioned adjacent the anesthesia side of one of the arm boards of the surgical table with the bulbous lower section fitting into the unused space under the arm board.

2c.) The module of any preceding example, configured so that the rear of the bulbous lower section can be accessed from the surgical side of the arm board for hose and electrical connections from the surgical field to the equipment contained in the module.

2d.) The module of any preceding example, wherein when the tower-like upper section is be positioned adjacent the anesthesia side of one of the arm boards of the surgical table with the bulbous lower section fitting into the unused space under the arm-board, the module can be accessed by staff simultaneously from both the anesthesia and surgical sides of the anesthesia screen.

2e.) The module of any preceding example, wherein the heavy electronic and electromechanical equipment is preferentially housed in the bulbous lower section, keeping the center of gravity close to the floor for added stability and tip resistance.

2f) The module of any preceding example, configured so that the tower-like upper section can accommodate the mounting of lightweight equipment controls, display screens and monitor screens at a convenient height for viewing and operating by a standing or sitting clinician.

In an example 3, a module for housing electronic and electromechanical equipment for use during surgery with a waste heat management system, the module comprising:
a lower section;
a tower-like upper section; and
the tower-like upper section is mounted on top of the lower section;
wherein at least some of the module and the equipment housed in the module is enclosed in a water-resistant cowling; and
air inlet vents in the cowling of the lower section allow air to enter and cool the electronic and electromechanical equipment housed in the lower section,
wherein the tower-like upper section serves as a chimney allowing a convection current of waste heat to rise within the tower-like upper section and escape from outlet vents located near the top of the tower-like upper section.

3a.) The module of any preceding example, wherein the lower section is a bulbous configuration so that the rear of the tower-like upper section can be positioned adjacent the anesthesia side of one of the arm-boards of the surgical table with the bulbous lower section fitting into the unused space under the arm board.

3b.) The module of any preceding example, wherein the top of the tower-like upper section is more than 4 feet above the floor.

3c.) The module of any preceding example, wherein one or more air filters are positioned adjacent the air inlet vents.

3d.) The module of any preceding example, wherein one or more air filters are positioned in the airflow path within the tower-like upper section.

3e.) The module of any preceding example, wherein a ventilation fan is positioned in the airflow path within the tower-like upper section.

In an example 4, a module for housing unrelated electronic and electromechanical equipment for use during surgery with a waste heat and air management system, the module comprising:
a bulbous lower section;
at least some of the module and the equipment housed in the module is enclosed in a water-resistant cowling;
a substantially vertical vent tube terminating at least 4 feet above the floor; and an air plenum in fluid communication with the substantially vertical vent tube;
one or more air inlets for allowing waste heat and air to enter the plenum; and
one or more air outlet vents near the distal top end of the substantially vertical vent tube, wherein an airflow path is created between the one or more air inlets, the plenum, the substantially vertical vent tube and the one or more air outlet vents;
a filter in the airflow path; and
a fan in the airflow path.

4a. The module of any preceding example, wherein the air inlet vents allow waste heat and air that cooled the electronic and electromechanical equipment housed in the bulbous lower section to enter the plenum for processing and safe discharge.

4b. The module of any preceding example, wherein the air inlet vents allow waste air from other sources such as surgical smoke evacuation and laminar ventilation dead zone evacuation to enter the plenum for processing and safe discharge.

4c. The module of any preceding example, wherein the air inlet vents allow waste heat and air from other sources such as forced-air warming to enter the plenum for processing and safe discharge.

4d. The module of any preceding example, wherein the substantially vertical vent tube is a rigid tube.

4e. The module of any preceding example, wherein the substantially vertical vent tube is an inflatable tube made of fabric, plastic film, plastic film laminated to fabric or other suitable materials.

4f. The module of any preceding example, including the inflatable substantially vertical vent tube of example 4e, wherein the air outlet vents near the distal top end of the inflatable tube are comprised of one or more holes which are sized to create a partial flow obstruction that increases the pressure within the inflatable tube and causes the inflatable tube to form a substantially erect shape rising upward from the module.

4g. The module of any preceding example, including the rigid substantially vertical vent tube of example 4d, wherein an inflatable tubular outlet vent extension made of fabric, plastic film, plastic film laminated to fabric or other suitable materials, may be attached to the distal top end of the rigid vent tube and extend substantially vertically, discharging the waste air from air outlet holes near the distal top end of the erect inflatable tube.

4h. The module of any preceding example, including the rigid substantially vertical vent tube of example 4d, wherein an inflatable tubular outlet vent extension made of fabric, plastic film, plastic film laminated to fabric or other suitable materials, may be attached to the distal top end of the rigid vent tube and extend at an upward angle, discharging the waste air from air outlet holes near the distal top end of the erect inflatable tube, outside of the operating room ventilation flow field.

In an example, 5, a module for housing unrelated electronic and electromechanical equipment for use during surgery, the module comprising:
 a lower section;
 a tower-like upper section; and
 the tower-like upper section being mounted on top of the lower section,
 wherein the tower-like upper section can be positioned adjacent the anesthesia side of one of the arm-boards of the surgical table with the lower section fitting into the unused space under and adjacent to the arm-board,
 the at least four sides of the module have independently unique and useful functions made possible by locating the module adjacent the arm board of the surgical table.

5a.) The module of any preceding example, configured so that the front face of the module is facing the anesthesia provider and therefore the equipment controls, display screens and monitor screens used by the anesthetist may advantageously be mounted on the front face of the module.

5b.) The module of any preceding example, configured so that the rear face of the tower-like upper section is facing the arm-board and from this location the lower section can be accessed from the surgical side of the anesthesia screen, for hose and electrical connections from the surgical field to the equipment contained in the module.

5c.) The module of any preceding example, configured so that the side of the module that is facing the patient and with the closest and most direct access to the patient, includes a cable and hose management system.

5d.) The module of any preceding example, wherein the cables and hoses are coiled and retained by an array of straps mounted on the side of the module.

5e.) The module of any preceding example, wherein the cables and hoses are coiled and retained by an array of hook-like protuberances mounted on the side of the module.

5f.) The module of any preceding example, wherein the cables and hoses are coiled and retained by an array of reels mounted on the side of the module.

5g.) The module of any preceding example, wherein the cables and hoses are manufactured as a coil and thus retain a spring-like configuration which can be stretched during use but returns to its natural spring-like shape when the tension on the cable or hose is released.

5h.) The module of any preceding example, wherein the wires of the cables are inserted into a plastic hose that has been manufactured in the form of a spring-like coil during the extrusion process and thus retains a spring-like configuration which can be stretched during use but returns to its natural spring-like shape when the tension on the cable or hose is released.

5i.) The module of any preceding example, configured so that the side of the module that is facing away from the patient and is thus easily accessed by the surgical nurse without disrupting the anesthetists work flow and therefore, the equipment controls, display screens and monitor screens used by the surgical nurse may advantageously be mounted on the side of the module facing away from the patient.

5j.) The module of any preceding example, wherein the lower section may protrude rearward from the rear plane of the tower-like upper section and when the rear plane of the tower-like upper section is positioned adjacent the anesthesia side of one of the arm-boards of the surgical table, the rearward protrusion of the lower section fits into the unused space under the arm-board allowing the module to be accessed by staff simultaneously from both the anesthesia and surgical sides of the anesthesia screen.

5k. The module of any preceding example, wherein at least some of the module and the equipment housed in the module is enclosed in a water-resistant cowling.

5l. The module of any preceding example, wherein water-resistant cowling is made of fiberglass, molded plastic, 3-D printed plastic, aluminum, stainless steel or other suitable water-resistant materials.

5m. The module of any preceding example, wherein the heavy electronic and electromechanical equipment is preferentially housed in the lower section, keeping the center of gravity close to the floor for added stability and tip resistance.

5n. The module of any preceding example, wherein the tower-like upper section can accommodate the mounting of lightweight equipment controls, display screens and monitor screens at a convenient height for viewing and operating by a standing or sitting anesthesia provider and surgical nurse.

5o. The module of any preceding example, wherein the top of the tower-like upper section is more than 4 feet above the floor.

5p. The module of any preceding example, configured so that power cables, communications cables, air hoses or vacuum hoses from the ceiling of the operating room can access the rack near the top of the tower-like upper section.

In an example 6, a module for housing electronic and electromechanical equipment for use during surgery with a cable and hose management system, the module comprising:
 a lower section;
 a tower-like upper section; and
 the tower-like upper section being mounted above the lower section,
 wherein the tower-like upper section can be positioned adjacent the anesthesia side of one of the arm-boards of the surgical table;
 wherein the side of the module that is facing the patient and with the closest and most direct access to the patient, includes a cable and hose management system,
 wherein at least a portion of the lower section fits into the unused space under the arm-board.

6a. The module and/or cable and hose management system any preceding example, wherein the cables and hoses are coiled and retained by an array of straps mounted on the side of the module.

6b. The module and/or cable and hose management system any preceding example, wherein the cables and hoses are coiled and retained by an array of hook-like protuberances mounted on the side of the module.

6c. The module and/or cable and hose management system any preceding example, wherein the cables and hoses are coiled and retained by an array of reels mounted on the side of the module.

6d. The module and/or cable and hose management system any preceding example, wherein the cables and hoses are manufactured as a coil and thus retain a spring-like configuration which can be stretched during use but returns to its natural spring-like shape when the tension on the cable or hose is released.

6e. The module and/or cable and hose management system any preceding example, wherein the cables are manufactured as a spring-like coil by extruding the outer electrically insulating layer of plastic in a coil form and thus the cables retain a spring-like configuration which can be stretched during use but returns to its natural spring-like shape when the tension on the cable or hose is released.

6f. The module and/or cable and hose management system any preceding example, wherein the wires of the cables are inserted into a plastic tubing that has been manufactured in the form of a spring-like coil during the extrusion process and thus retains a spring-like configuration which can be stretched during use but returns to its natural spring-like shape when the tension on the cable or hose is released.

6g. The module and/or cable and hose management system any preceding example, wherein the outer surface of the cables or hoses in coil form are made from extruded urethane, nylon, PVC or other suitable plastics.

6h. The module and/or cable and hose management system any preceding example, wherein the coils are 1.5-6 inches in diameter.

6i. The module and/or cable and hose management system any preceding example, wherein some or all of the module and the equipment housed in the module is enclosed in a water-resistant cowling and the cable and hose management system is incorporated into the cowling on one or more faces of the module.

In an example 7, a module for housing equipment for use during surgery with access from both the surgical and anesthesia sides of the anesthesia screen, the module comprising:
 a bulbous lower section; and
 an upper section;
 the upper section being mounted on the front portion of the bulbous lower section,
 the upper section can be accessed by the anesthesia provider from the anesthesia side of the anesthesia screen for hose and electrical connections from the patient to the equipment contained in the module, and
 the rear portion of the bulbous lower section is configured to fit under an over-hanging obstruction such as the arm-board of the surgical table,
 wherein the rear of the bulbous lower section can be simultaneously accessed by the surgical staff from the surgical side of the anesthesia screen for hose and electrical connections from the surgical field to the equipment contained in the module.

7a. The module of any preceding example, configured so that the rear of the upper section can be positioned adjacent the anesthesia side of one of the arm-boards of the surgical table with the bulbous lower section fitting into the unused space under the arm-board.

7b. The module of any preceding example, configured so that the rear of the bulbous lower section includes the connectors for the cables and hoses extending off of the sterile surgical field.

7c. The module of any preceding example, configured so that cables and hoses draping off of the head end of the sterile surgical field adjacent the anesthesia screen, drop substantially straight downward to engage the connectors for the cables and hoses located on the rear of the bulbous lower section.

7d. The module of example 7c, wherein the cables and hoses draping off of the head end of the sterile surgical field adjacent the anesthesia screen and dropping substantially straight downward to engage the connectors for the cables and hoses located on the rear of the bulbous lower section do not touch the floor of the operating room.

7e. The module of any preceding example, configured so that the connectors for the cables are located on the vertical face of the rear of the bulbous lower section to prevent fluid ingress into the electrical connection.

7f. The module of any preceding example, configured so that the connectors for the hoses are located on the bulbous lower section near the top of the side facing away from the patient to prevent hose kinking and to help keep the hose off of the floor.

7g. The module of any preceding example, wherein the upper section can accommodate the mounting of lightweight equipment controls, display screens and monitor screens at a convenient height for viewing and operating.

7h. The module of any preceding example, configured to include a cradle area on the side of the module for seating one or more blood/fluid suction canisters.

7i. The module of any preceding example, configured to include a vacuum management system to control the vacuum in the one or more blood/fluid suction canisters and prevent blood/fluid from contaminating the hospital vacuum system.

In an example method 8, the method includes storing at least one piece of anesthesia related equipment (e.g., can include monitoring) in a module according to any of the preceding examples or embodiments described herein. The method can also include storing at least one piece of dissimilar operating room equipment related to surgical aspects of the operating room in the module with the at least one piece of anesthesia related equipment. The method can further include collecting waste heat from two or more pieces of equipment in the module, and discharging the waste heat above the height of the equipment, or discharging the waste heat above the height of the module.

The example of claim 8, wherein the dissimilar operating room equipment can be any of the equipment described herein.

What is claimed is:

1. A module for housing electronic and electromechanical equipment during surgery, the module comprising:
 a lower section configured to house unrelated waste heat-producing electronic and electromechanical surgical equipment during surgery, wherein a rear portion of the lower section is configured to fit into an unused space under an arm-board of a surgical table; and
 a tower-like upper section located above the lower section,
 wherein the upper section is configured to be positioned adjacent an anesthesia side of an arm-board of the surgical table,
 wherein the upper section is configured to accommodate mounting of equipment controls and a display at a height to be viewed and operated by a user.

2. The module of claim 1, wherein the equipment controls include at least one of: a keyboard and mouse for data entry to enter data into an anesthetic record.

3. The module of claim 1, wherein the waste heat-producing electronic and electromechanical surgical equipment includes electronics for a patient monitor that generates data to be stored in an anesthetic record.

4. The module of claim 1, further comprising:
a display mounted on the upper section, wherein the display is configured to be in wireless communication with a remotely located patient monitor to display output of the patient monitor.

5. The module of claim 1, wherein one or more warning lights are mounted on the upper section or on a patient monitor display that is mounted on the upper section and the one or more warning lights is aimed away from the upper section toward an anesthesia provider position.

6. The module of claim 5, wherein the one or more warning lights are activated as a primary alarm for a patient malfunction or an equipment malfunction without activating an audible alarm.

7. The module of claim 5, wherein the one or more warning lights are color-coded to indicate a patient malfunction or an equipment malfunction.

8. The module of claim 6, wherein an audible secondary alarm is activated if the user does not physically acknowledge the primary alarm within a given period of time.

9. The module of claim 1, wherein the module includes components of an anesthetic gas machine.

10. The module of claim 9, wherein the components of the anesthetic gas machine include piping, valves, flow meters, vaporizers and a patient ventilator.

11. The module of claim 9, wherein the components of the anesthetic gas machine include a pressurizable gas tank to store at least one of: oxygen, nitrous oxide and air, and wherein the pressurizable gas tank is attached to the lower section.

12. The module of claim 9, wherein the components of the anesthetic gas machine include a pressurized gas connector on the upper section, the pressurized gas connector configured to connect to a gas hose hanging from a ceiling of an operating room.

13. A module for housing electronic and electromechanical equipment during surgery, the module comprising:
a lower section configured to house unrelated waste heat-producing electronic and electromechanical surgical equipment during surgery;
a tower-like upper section located above the lower section, wherein the upper section is configured to be positioned adjacent an anesthesia side of an arm-board of a surgical table;
a cable and hose management system located on a patient side of the module, wherein the patient side of the module is configured to face a patient and provide the closest and most direct access to a patient when the module is positioned adjacent the anesthesia side of the arm-board of the surgical table; and
the upper section is configured to accommodate mounting of equipment controls and a display at a height to be viewed and operated by a user.

14. The module of claim 13, wherein the equipment controls include at least one of a keyboard and a mouse pad to enter data to an anesthetic record.

15. The module of claim 13, wherein the waste heat-producing electronic and electromechanical surgical equipment includes electronics for a patient monitor that generates data to be stored in an anesthetic record.

16. The module of claim 13, further comprising:
a display mounted on the upper section, wherein the display is configured to be in wireless communication with a remotely located patient monitor to display output of the patient monitor.

17. The module of claim 13, wherein one or more warning lights are mounted on the upper section or on a patient monitor display screen that is mounted on the upper section and the light is aimed away from the upper section toward an anesthesia provider position.

18. The module of claim 17, wherein the one or more warning lights are activated as a primary alarm for a patient malfunction or an equipment malfunction, without activating an audible alarm.

19. The module of claim 17, wherein the one or more warning lights are color-coded to indicate a patient malfunction or an equipment malfunction.

20. The module of claim 18, wherein an audible secondary alarm is activated if the user does not physically acknowledge the primary alarm within a given period of time.

21. The module of claim 13, wherein the module includes components of an anesthetic gas machine.

22. The module of claim 21, wherein the components of the anesthetic gas machine include piping, valves, flow meters, vaporizers and a patient ventilator.

23. The module of claim 21, wherein the components of the anesthetic gas machine include a pressurizable gas tank to store at least one of: oxygen, nitrous oxide and, and wherein the pressurizable gas tank is attached to the lower section.

24. The module of claim 21, wherein the components of the anesthetic gas machine include a pressurized gas connector on the upper section configured to connect to a gas hose hanging from a ceiling of an operating room.

25. A module for housing unrelated electronic and electromechanical surgical equipment and for managing waste heat during surgery, the module comprising:
a lower section configured to house unrelated waste heat-producing electronic and electromechanical surgical equipment;
a tower-like upper section located on top of the lower section;
a cowling that substantially confines waste heat generated by the unrelated waste heat-producing electronic and electromechanical surgical equipment; and
the upper section is configured to accommodate mounting of equipment controls and a display at a height to be viewed and operated by a user.

* * * * *